United States Patent
Umetani et al.

(10) Patent No.: US 7,786,040 B2
(45) Date of Patent: Aug. 31, 2010

(54) 4-CYCLOPROPYL-1,2,3,-THIADIAZOLE COMPOUND, AGROHORTICULTURAL PLANT DISEASE CONTROLLING AGENT AND METHOD OF USING THE SAME

(75) Inventors: Kunihisa Umetani, Osaka (JP); Takashi Shimaoka, Osaka (JP); Minoru Yamaguchi, Osaka (JP); Masatsugu Oda, Osaka (JP); Nobuo Kyomura, Osaka (JP); Tsuyoshi Takemoto, Osaka (JP); Kazuhiko Kikutake, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 20 days.

(21) Appl. No.: 11/817,082

(22) PCT Filed: Feb. 23, 2006

(86) PCT No.: PCT/JP2006/303313

§ 371 (c)(1),
(2), (4) Date: Aug. 24, 2007

(87) PCT Pub. No.: WO2006/098128

PCT Pub. Date: Sep. 21, 2006

(65) Prior Publication Data

US 2008/0200457 A1    Aug. 21, 2008

(30) Foreign Application Priority Data

Feb. 24, 2005  (JP) ............... 2005-049431
Sep. 12, 2005  (JP) ............... 2005-263617

(51) Int. Cl.
*A01N 25/02*  (2006.01)
*A01N 25/08*  (2006.01)
*A01N 43/828* (2006.01)
*A61K 31/433* (2006.01)
*C07D 285/06* (2006.01)

(52) U.S. Cl. .............. 504/100; 504/261; 514/361; 548/127

(58) Field of Classification Search ............... 548/127; 514/361; 504/100, 261
See application file for complete search history.

(56) References Cited

U.S. PATENT DOCUMENTS 6,166,054 A * 12/2000 Kuroda et al. ............... 514/361

FOREIGN PATENT DOCUMENTS

| JP | 8 325110 | 12/1996 |
|----|----------|---------|
| JP | 10 152482 | 6/1998 |
| JP | 2000 501102 | 2/2000 |
| JP | 2000 501400 | 2/2000 |
| JP | 2000 103710 | 4/2000 |
| JP | 2000-169461 A | 6/2000 |
| JP | 2001 10909 | 1/2001 |
| JP | 2001 139566 | 5/2001 |

* cited by examiner

*Primary Examiner*—Rebecca L Anderson
*Assistant Examiner*—Shawquia Young
(74) *Attorney, Agent, or Firm*—Oblon, Spivak, Maier & Neustadt, L.L.P.

(57) ABSTRACT

The present invention relates to 1,2,3-thiadiazole compounds represented by formula (I):

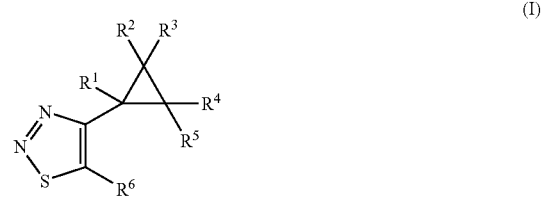

wherein $R^1$, $R^2$, $R^3$, $R^4$ and $R^5$ each represents H, halogen, CN, alkyl, alkoxyalkyl, aryl, arylalkyl, alkylcarbonyl or the like; $R^6$ represents $-C=(W^1)YR^7$ in which $R^7$ represents H, alkyl, alkenyl, phenylcarbonyl, heterocyclic ring-carbonyl, arylsulfonyl or the like; Y represents O, S, $-N(R^{11})$, $-N(R^{11})O-$ in which $R^{11}$ represents H, alkyl, cycloalkyl, substituted phenyl, or the like; $W^1$ represents O or S; and symbols in the formula are defined in detail in the specification or salts thereof, and to a plant disease control agent for agricultural and horticultural use which contains the compound as an active ingredient.

22 Claims, No Drawings

4-CYCLOPROPYL-1,2,3,-THIADIAZOLE COMPOUND, AGROHORTICULTURAL PLANT DISEASE CONTROLLING AGENT AND METHOD OF USING THE SAME

TECHNICAL FIELD

The present invention relates to 4-cyclopropyl-1,2,3-thiadiazole compounds or salts thereof, plant disease control agents for agricultural and horticultural use containing the compound as an active ingredient, and methods of using the same. Furthermore, it also relates to plant disease control agents for the treatment of seeds of objective plants or a cultivation carrier for sowing objective plants, and to a method of using them.

BACKGROUND OF THE INVENTION

Still now, agricultural and horticultural production is seriously damaged by diseases, and there exists a factor of chemical resistance acquired by microorganisms and fungi against existing chemicals. Thus, it has been desired to develop novel plant disease control agents for agricultural and horticultural use. Therefore, many agents for controlling plant diseases have so far been investigated and developed and have been used according to application methods adapted for respective chemicals. In recent years, various labor-saving methods of applying chemicals have been required with the advance of age of farmers, and reduction in amount of chemical to be used has been required for the purpose of preserving earth environment. Hence, developments of plant disease control agents for agricultural and horticultural use and methods of using them which can meet the requirements have strongly been demanded. As one of using methods of applying a plant disease control agent for agricultural and horticultural use, there has been known a method of applying the agent to seeds of objective plants or to a cultivation carrier for sowing objective plants. This method has the advantage that, since it requires the chemical to exist only around the seeds of the objective plant or around the cultivation carrier for sowing the objective plant, it leads to reduction of the amount of chemicals to be used, serves to reduce the load to earth environment and, further, reduces contact between workers and chemicals so as to increase safety of workers and leads to saving of works.

Under such circumstances, certain kinds of 1,2,3-thiadiazole compounds are described to be useful as plant disease control agents for agricultural and horticultural use (for example, see patent document 1). However, there has been neither description nor suggestion about use of the 4-cyclopropyl-1,2,3-thiadiazole compounds of the invention represented by formula (I) as agents for controlling plant diseases or methods of applying the controlling agents to seeds of objective plants or to a cultivation carrier for sowing the objective plant. Also, there is no specific description about the 4-cyclopropyl-1,2,3-thiadiazole compounds of the invention represented by formula (I). On the other hand, there has been described a method of applying specific 1,2,3-thiadiazole compounds to seeds of an objective plant or to a cultivation carrier for sowing an objective plant (for example, see patent document 2). In patent document 2, however, there is only one compound as Example and, with regard to 4-cyclopropane compounds, although two compounds are described in the compound list, there are no Examples demonstrating that the compounds are actually effective, and there are absolutely no disclosure in the document about the specifically excellent effect provided by using the 4-cyclopropyl-1,2,3-thiadiazole compounds of the invention represented by formula (I) according to the present method of use.

Patent document 1: JP-A-8-325110
Patent document 2: JP-A-2001-10909

DISCLOSURE OF THE INVENTION

As is described hereinbefore, there has been a demand for plant disease control agents for agricultural and horticultural use which can be used as plant disease control agents for agricultural and horticultural use and which, at the same time, are particularly adapted for a method of applying to seeds of the objective plant or to a cultivation carrier for sowing the objective plant and for a using method of applying to seeds of the objective plant or to a cultivation carrier for sowing the objective plant. However, the above-mentioned background art involves the problem that sufficient performance cannot be obtained with respect to fungicidal spectrum, amount of a chemical to be used, long-lasting effect and safety to objective plants. In particular, in the conventional art, it has been intended to control diseases up to the initial growth stage of objective plants, and therefore it has been necessary to apply different plant disease controlling agents in the following stage of from the highest growth stage to the latter stage. Thus, there has been a demand for a plant disease control agent for agricultural and horticultural use which shows a long-lasting effect over a long period of from the highest growth stage to the latter stage.

As a result of intensive investigations to solve the above-mentioned problems, the inventors have found that 4-cyclopropyl-1,2,3-thiadiazole compounds represented by formula (I) not only have an excellent safety to objective plants and an excellent controlling effect on various plant diseases but have an extremely long-lasting effect, thus having completed the invention. In particular, when the compound of the invention is applied to seeds of the objective plant or to a cultivation carrier for sowing the objective plant, plant diseases can be controlled over a long period of from the highest growth stage to the latter growth stage, which cannot be expected from the aforementioned conventional art.

That is, the invention relates to (1) to (13) described below.
(1) A 1,2,3-thiadiazole compound represented by formula (I)

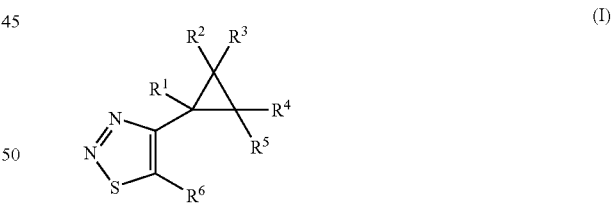

wherein $R^1$, $R^2$, $R^3$, $R^4$ and $R^5$ are the same or different and each represents a hydrogen atom; a halogen atom; cyano; $(C_1-C_6)$alkyl; halo$(C_1-C_6)$alkyl; $(C_1-C_6)$alkoxy$(C_1-C_6)$alkyl; $(C_3-C_{12})$cycloalkyl; halo$(C_3-C_{12})$cycloalkyl; $(C_1-C_6)$alkylthio$(C_1-C_6)$alkyl; $(C_2-C_6)$alkenyl; halo$(C_2-C_6)$alkenyl; aryl which may be substituted with a substituent Z; aryl$(C_1-C_6)$alkyl which may be substituted on its ring with a substituent Z; or $(C_1-C_6)$alkylcarbonyl, $R^6$ represents:
(a) —C(=W$^1$)YR$^7$
wherein $R^7$ represents a hydrogen atom; $(C_1-C_{20})$alkyl; halo$(C_1-C_{20})$alkyl; $(C_2-C_{20})$alkenyl; halo$(C_2-C_{20})$alkenyl; $(C_2-C_{20})$alkynyl; halo$(C_2-C_{20})$alkynyl; $(C_3-C_{12})$cycloalkyl; halo$(C_3-C_{12})$cycloalkyl; $(C_1-C_6)$alkoxy$(C_1-C_6)$alkyl; $(C_1-$ $C_6$)alkylthio($C_1$-$C_6$)alkyl; aryl($C_1$-$C_6$)alkyl which may be substituted on its ring with a substituent Z; aryloxy($C_1$-$C_6$) alkyl which may be substituted on its ring with a substituent Z; arylthio($C_1$-$C_6$)alkyl which may be substituted on its ring with a substituent Z; aryl which may be substituted with a substituent Z; carboxy($C_1$-$C_6$)alkyl; ($C_1$-$C_6$)alkoxycarbonyl ($C_1$-$C_6$)alkyl; carbamoyl($C_1$-$C_6$)alkyl; carbamoyl($C_1$-$C_6$) alkyl, having on the nitrogen atom, 1 or 2 substituents which are the same or different and are selected from ($C_1$-$C_{10}$)alkyl, halo($C_1$-$C_{10}$)alkyl, ($C_2$-$C_{10}$)alkenyl, ($C_3$-$C_{10}$)cycloalkyl, phenyl which may be substituted with a substituent Z, or phenyl($C_1$-$C_6$)alkyl which may be substituted on its ring with a substituent Z; cyano($C_1$-$C_6$)alkyl; a heterocyclic ring which may be substituted with a substituent Z; heterocyclic ($C_1$-$C_6$) alkyl which may be substituted on its ring with a substituent Z; ($C_1$-$C_{20}$)alkylcarbonyl; ($C_2$-$C_{20}$)alkynylcarbonyl; ($C_2$-$C_6$) alkenylcarbonyl; ($C_3$-$C_6$)cycloalkylcarbonyl; phenylcarbonyl which may be substituted with a substituent Z; heterocyclic carbonyl which may be substituted with a substituent Z; ($C_1$-$C_{20}$)alkylsulfonyl; halo($C_1$-$C_{20}$)alkylsulfonyl; arylsulfonyl which may be substituted with a substituent Z; aryl($C_1$-$C_6$)alkylsulfonyl which may be substituted on its ring with a substituent Z; —C(=$W^2$)$NR^8R^9$ wherein $R^8$ and $R^9$ are the same or different and each represents a hydrogen atom, ($C_1$-$C_{10}$)alkyl, halo($C_1$-$C_{10}$)alkyl, ($C_2$-$C_{10}$)alkenyl, ($C_3$-$C_{10}$)cycloalkyl, phenyl which may be substituted with a substituent Z, phenyl($C_1$-$C_6$)alkyl which may be substituted on its ring with a substituent Z, ($C_1$-$C_6$)alkoxy, phenoxy which may be substituted with a substituent Z or phenyl($C_1$-$C_6$)alkyloxy which may be substituted on its ring with a substituent Z, or $R^8$ and $R^9$ may be taken together to form ($C_2$-$C_6$)alkylene which may be interrupted by an oxygen atom, an sulfur atom or $NR^{10}$ wherein $R^{10}$ represents a hydrogen atom, ($C_1$-$C_6$) alkyl or phenyl which may be substituted with a substituent Z, and $W^2$ represents an oxygen atom or a sulfur atom; —$SO_2NR^8R^9$ wherein $R^8$ and $R^9$ have the same meanings as defined above; or —N=C($R^8$)$R^9$ wherein $R^8$ and $R^9$ have the same meanings as defined above, Y represents an oxygen atom; a sulfur atom; —N($R^{11}$)— wherein $R^{11}$ represents a hydrogen atom, ($C_1$-$C_6$)alkyl, ($C_3$-$C_6$)cycloalkyl, phenyl which may be substituted with a substituent Z, phenyl($C_1$-$C_6$)alkyl which may be substituted with a substituent Z, ($C_1$-$C_{10}$)alkylcarbonyl, ($C_2$-$C_{10}$)alkynylcarbonyl, ($C_2$-$C_{10}$)alkenylcarbonyl, ($C_3$-$C_6$)cycloalkylcarbonyl, phenylcarbonyl which may be substituted with a substituent Z, or heterocyclic ring-carbonyl which may be substituted with a substituent Z; or —N($R^{11}$)O— wherein $R^{11}$ has the same meaning as defined above, and $W^1$ represents an oxygen atom or a sulfur atom, (b) a group represented by the following formula

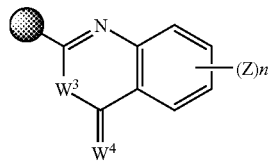

wherein n represents an integer of from 0 to 4, and $W^3$ and $W^4$ are the same or different and each represents an oxygen atom or a sulfur atom, or (c) cyano, Z's are the same or different and each represents one or more substituents selected from a halogen atom; hydroxyl; cyano; nitro; ($C_1$-$C_6$)alkyl; halo($C_1$-$C_6$)alkyl; ($C_3$-$C_{12}$)cycloalkyl; halo($C_3$-$C_{12}$)cycloalkyl; phenyl which may be substituted with 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo ($C_1$-$C_6$)alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X which are the same or different on the nitrogen atom; phenyl($C_1$-$C_6$)alkyl which may have on its ring from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X which are the same or different on the nitrogen atom; ($C_1$-$C_6$) alkoxy; halo($C_1$-$C_6$)alkoxy; ($C_1$-$C_6$)alkylthio; halo($C_1$-$C_6$) alkylthio; ($C_1$-$C_6$)alkylsulfinyl; halo($C_1$-$C_6$)alkylsulfinyl; ($C_1$-$C_6$)alkylsulfonyl; halo($C_1$-$C_6$)alkylsulfonyl; phenoxy which may have from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X which are the same or different on the nitrogen atom; phenylthio which may have from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$) alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X on the nitrogen atom; phenylsulfinyl which may have from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X on the nitrogen atom; phenylsulfonyl which may have from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, halo($C_1$-$C_6$)alkylthio, carboxyl, ($C_1$-$C_6$) alkoxycarbonyl, carbamoyl and substituted carbamoyl having a substituent(s) X on the nitrogen atom; phenyl($C_1$-$C_6$) alkyloxy which may have on its ring from 1 to 5 substituents which are the same or different and are selected from a halogen atom, hydroxyl, cyano, nitro, ($C_1$-$C_6$)alkyl, halo($C_1$-$C_6$) alkyl, ($C_1$-$C_6$)alkoxy, halo($C_1$-$C_6$)alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X on the nitrogen atom; carboxyl; ($C_1$-$C_6$)alkoxycarbonyl; carbamoyl which may be substituted with a substituent(s) X; ($C_1$-$C_6$)alkylcarbonyl or phenylcarbonyl which may have from 1 to 5 substituents which are the same or different and are selected from a halogen atom, hydroxyl, cyano, nitro, ($C_1$-$C_6$)alkyl, halo($C_1$-$C_6$)alkyl, ($C_1$-$C_6$)alkoxy, halo($C_1$-$C_6$) alkoxy, ($C_1$-$C_6$)alkylthio, halo($C_1$-$C_6$)alkylthio, carboxyl, ($C_1$-$C_6$)alkoxycarbonyl, carbamoyl and substituted carbamoyl having a substituent(s) X on the nitrogen atom;

X represents ($C_1$-$C_{10}$)alkyl; halo($C_1$-$C_{10}$)alkyl; phenyl which may have from 1 to 5 substituents which are the same or different and are selected from a halogen atom, cyano, nitro, ($C_1$-$C_6$)alkyl, halo($C_1$-$C_6$)alkyl, ($C_1$-$C_6$)alkoxy, halo ($C_1$-$C_6$)alkoxy, ($C_1$-$C_6$)alkylthio or halo($C_1$-$C_6$)alkylthio; or phenyl($C_1$-$C_6$)allyl which may have on its ring from 1 to 5 substituents which are the same or different and are selected from a halogen atom, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio or halo$(C_1-C_6)$alkylthio, and wherein 4-cyclopropyl-1,2,3-thiadiazole-5-carboxylic acid, methyl 4-cyclopropyl-1,2,3-thiadiazole-5-carboxylate, ethyl 4-cyclopropyl-1,2,3-thiadiazole-5-carboxylate, benzyl 4-cyclopropyl-1,2,3-thiadiazole-5-carboxylate, 4-cyclopropyl-1,2,3-thiadiazole-5-carboxamide, 4-cyclopropyl-1,2,3-thiadiazole-5-carboxanilide, 4-cyclopropyl-3'-isopropyl-1,2,3-thiadiazole-5-carboxanilide, 4-cyclopropyl-3'-isopropoxy-1,2,3-thiadiazole-5-carboxanilide and 4-cyclopropyl-5-(1,3-dithiolan-2-ylidenaminocarbonitrile)-1,2,3-thiadiazole are excluded, or a salt thereof.

(2) The 1,2,3-thiadiazole compound according to (1), wherein $R^1$, $R^2$, $R^3$, $R^4$ and $R^5$ are the same or different and each represents a hydrogen atom; a halogen atom; $(C_1-C_6)$alkyl; halo$(C_1-C_6)$alkyl; $(C_2-C_6)$alkenyl; halo$(C_2-C_6)$alkenyl; phenyl or substituted phenyl which may have 1 to 5 substituents Z which are the same or different; or a salt thereof.

(3) The 1,2,3-thiadiazole compound according to (1), wherein $R^1$, $R^2$, $R^3$, $R^4$ and $R^5$ each represents a hydrogen atom, and $R^6$ represents —C(=W$^1$)YR$^7$ wherein $R^7$ represents $(C_3-C_{10})$alkyl or substituted phenyl $(C_1-C_6)$alkyl having on its ring one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and $(C_1-C_6)$alkoxycarbonyl, and W$^1$ and Y represent an oxygen atom, or a salt thereof.

(4) The 1,2,3-thiadiazole compound according to (1), wherein $R^1$, $R^2$, $R^3$, $R^4$ and $R^5$ each represents a hydrogen atom, and $R^6$ represents —C(=W$^1$)YR$^7$ wherein $R^7$ represents $(C_1-C_6)$alkyl; substituted phenyl $(C_1-C_6)$alkyl having on its ring one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and $(C_1-C_6)$alkoxycarbonyl; substituted phenyl having one or more substituents which are the same or different and are selected from a halogen atom, cyano, methyl, ethyl, n-propyl, n-butyl, t-butyl, halo$(C_1-C_6)$alkyl, methoxy, ethoxy, halo$(C_1-C_6)$alkoxy and $(C_1-C_6)$alkoxycarbonyl; thiazolyl; substituted thiazolyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl; benzothiazolyl; substituted benzothiazolyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl; pyrimidyl; substituted pyrimidyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl; phenylsulfonyl; or phenylsulfonyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl, W$^1$ represents an oxygen atom, and Y represents —NH—, or a salt thereof.

(5) The 1,2,3-thiadiazole compound according to (1), which is selected from octyl 4-cyclopropyl-1,2,3-thiadiazole-5-carboxylate, (2-chlorobenzyl)4-cyclopropyl-1,2,3-thiadiazole-5-carboxylate, (3-chlorobenzyl)4-cyclopropyl-1,2,3-thiadiazole-5-carboxylate, (4-chlorobenzyl)4-cyclopropyl-1,2,3-thiadiazole-5-carboxylate, (4-chloro-α-methylbenzyl)4-cyclopropyl-1,2,3-thiadiazole-5-carboxylate, (4-methoxycarbonylbenzyl)4-cyclopropyl-1,2,3-thiadiazole-5-carboxylate, N-benzyl-4-cyclopropyl-1,2,3-thiadiazole-5-carboxamide, N-(4-t-butylbenzyl)-4-cyclopropyl-1,2,3-thiadiazole-5-carboxamide, 3'-chloro-4-cyclopropyl-4'-methyl-1,2,3-thiadiazole-5-carboxanilide, 4-cyclopropyl-2',4'-dimethoxy-1,2,3-thiadiazole-5-carboxanilide, 4-cyclopropyl-3',4'-dimethoxy-1,2,3-thiadiazole-5-carboxanilide, 2'-carboxy-4-cyclopropyl-1,2,3-thiadiazole-5-carboxanilide, N-(4-isobutylthiazol-2-yl)-4-cyclopropyl-1,2,3-thiadiazole-5-carboxamide, N-phenylsulfonyl-4-cyclopropyl-1,2,3-thiadiazole-5-carboxamide, N-(3,4-dimethoxybenzyl)-4-cyclopropyl-1,2,3-thiadiazole-5-carboxamide, 2-(4-cyclopropyl-1,2,3-thiadiazol-5-yl)-4H-3,1-benzoxazin-4-one, or a salt thereof.

(6) A plant disease control agent for agricultural and horticultural use, which comprises as an active ingredient the 1,2,3-thiadiazole compound according to any one of (1) to (5) or a salt thereof.

(7) A plant disease control agent for agricultural and horticultural use for sterilizing seeds, which comprises as an active ingredient one or two or more compounds selected from 1,2,3-thiadiazole compounds represented by the formula (I)

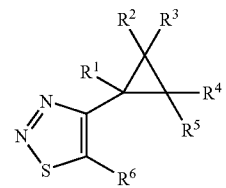

(I)

wherein $R^1$, $R^2$, $R^3$, $R^4$ and $R^5$ are the same or different and each represents a hydrogen atom; a halogen atom; cyano; $(C_1-C_6)$alkyl; halo$(C_1-C_6)$alkyl; $(C_1-C_6)$alkoxy$(C_1-C_6)$alkyl; $(C_3-C_{12})$cycloalkyl; halo$(C_3-C_{12})$cycloalkyl; $(C_1-C_6)$alkylthio$(C_1-C_6)$alkyl; $(C_2-C_6)$alkenyl; halo$(C_2-C_6)$alkenyl; aryl which may be substituted with a substituent Z; aryl$(C_1-C_6)$alkyl which may be substituted on its ring with a substituent Z or $(C_1-C_6)$alkylcarbonyl, $R^6$ represents:

(a) —C(=W$^1$)YR$^7$ wherein $R^7$ represents a hydrogen atom; $(C_1-C_{20})$alkyl; halo$(C_1-C_{20})$alkyl; $(C_2-C_{20})$alkenyl; halo$(C_2-C_{20})$alkenyl; $(C_2-C_{20})$alkynyl; halo$(C_2-C_{20})$alkynyl; $(C_3-C_{12})$cycloalkyl; halo$(C_3-C_{12})$cycloalkyl; $(C_1-C_6)$alkoxy$(C_1-C_6)$alkyl; $(C_1-C_6)$alkylthio$(C_1-C_6)$alkyl; aryl$(C_1-C_6)$alkyl which may be substituted on its ring with a substituent Z; aryloxy$(C_1-C_6)$alkyl which may be substituted on its ring with a substituent Z; arylthio$(C_1-C_6)$alkyl which may be substituted on its ring with a substituent Z; aryl which may be substituted with a substituent Z; carboxy$(C_1-C_6)$alkyl; $(C_1-C_6)$alkoxycarbonyl$(C_1-C_6)$alkyl; carbamoyl$(C_1-C_6)$alkyl; carbamoyl$(C_1-C_6)$alkyl, having on the nitrogen atom, 1 or 2 substituents which are the same or different and are selected from $(C_1-C_{10})$alkyl, halo$(C_1-C_{10})$alkyl, $(C_2-C_{10})$alkenyl, $(C_3-C_{10})$cycloalkyl, phenyl which may be substituted with a substituent Z, or phenyl$(C_1-C_6)$alkyl which may be substituted on its ring with a substituent Z; cyano$(C_1-C_6)$alkyl; a heterocyclic ring which may be substituted with a substituent Z; heterocyclic $(C_1-C_6)$alkyl which may be substituted on its ring with a substituent Z; $(C_1-C_{20})$alkylcarbonyl; $(C_2-C_{20})$alkynylcarbonyl; $(C_2-C_6)$ alkenylcarbonyl; $(C_3-C_6)$cycloalkylcarbonyl; phenylcarbonyl which may be substituted with a substituent Z; heterocyclic carbonyl which may be substituted with a substituent Z; $(C_1-C_{20})$alkylsulfonyl; halo$(C_1-C_{20})$alkylsulfonyl; arylsulfonyl which may be substituted with a substituent Z; aryl$(C_1-C_6)$alkylsulfonyl which may be substituted on its ring with a substituent Z; —C(=$W^2$)$NR^8R^9$ wherein $R^8$ and $R^9$ are the same or different and each represents a hydrogen atom, $(C_1-C_{10})$alkyl, halo$(C_1-C_{10})$alkyl, $(C_2-C_{10})$alkenyl, $(C_3-C_{10})$cycloalkyl, phenyl which may be substituted with a substituent Z, phenyl$(C_1-C_6)$alkyl which may be substituted on its ring with a substituent Z, $(C_1-C_6)$alkoxy, phenoxy which may be substituted with a substituent Z or phenyl$(C_1-C_6)$alkyloxy which may be substituted on its ring with a substituent Z, or $R^8$ and $R^9$ may be taken together to form $(C_2-C_6)$alkylene which may be interrupted by an oxygen atom, an sulfur atom or $NR^{10}$ wherein $R^{10}$ represents a hydrogen atom, $(C_1-C_6)$alkyl or phenyl which may be substituted with a substituent Z, and $W^2$ represents an oxygen atom or a sulfur atom; —SO$_2NR^8R^9$ wherein $R^8$ and $R^9$ have the same meanings as defined above or —N=C($R^8$)$R^9$ wherein $R^8$ and $R^9$ have the same meanings as defined above, Y represents an oxygen atom; a sulfur atom; —N($R^{11}$)— wherein $R^{11}$ represents a hydrogen atom, $(C_1-C_6)$alkyl, $(C_3-C_6)$cycloalkyl, phenyl which may be substituted with a substituent Z, phenyl$(C_1-C_6)$alkyl which may be substituted with a substituent Z, $(C_1-C_{10})$alkylcarbonyl, $(C_2-C_{10})$alkynylcarbonyl, $(C_2-C_{10})$alkenylcarbonyl, $(C_3-C_6)$cycloalkylcarbonyl, phenylcarbonyl which may be substituted with a substituent Z or heterocyclic ring-carbonyl which may be substituted with a substituent Z; or —N($R^{11}$)O— wherein $R^{11}$ has the same meaning as defined above, and $W^1$ represents an oxygen atom or a sulfur atom, (b) a group represented by the following formula

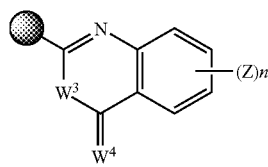

wherein n represents an integer of from 0 to 4, and $W^3$ and $W^4$ are the same or different and each represents an oxygen atom or a sulfur atom, or (c) cyano, Z's are the same or different and each represents one or more substituents selected from a halogen atom; hydroxyl; cyano; nitro; $(C_1-C_6)$alkyl; halo$(C_1-C_6)$alkyl; $(C_3-C_{12})$cycloalkyl; halo$(C_3-C_{12})$cycloalkyl; phenyl which may be substituted with 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X which are the same or different on the nitrogen atom; phenyl$(C_1-C_6)$alkyl which may have on its ring from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X which are the same or different on the nitrogen atom; $(C_1-C_6)$alkoxy; halo$(C_1-C_6)$alkoxy; $(C_1-C_6)$alkylthio; halo$(C_1-C_6)$alkylthio; $(C_1-C_6)$alkylsulfinyl; halo$(C_1-C_6)$alkylsulfinyl; $(C_1-C_6)$alkylsulfonyl; halo$(C_1-C_6)$alkylsulfonyl; phenoxy which may have from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X which are the same or different on the nitrogen atom; phenylthio which may have from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X on the nitrogen atom; phenylsulfinyl which may have from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X on the nitrogen atom; phenylsulfonyl which may have from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X on the nitrogen atom; phenyl$(C_1-C_6)$alkyloxy which may have on its ring from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X on the nitrogen atom; carboxyl; $(C_1-C_6)$alkoxycarbonyl; carbamoyl which may be substituted with a substituent(s) X; $(C_1-C_6)$alkylcarbonyl or phenylcarbonyl which may have from 1 to 5 substituents which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and substituted carbamoyl having a substituent(s) X on the nitrogen atom;

X represents $(C_1-C_{10})$alkyl; halo$(C_1-C_{10})$alkyl; phenyl which may have from 1 to 5 substituents which are the same or different and are selected from a halogen atom, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio or halo$(C_1-C_6)$alkylthio; or phenyl$(C_1-C_6)$alkyl which may have on its ring from 1 to 5 substituents which are the same or different and are selected from a halogen atom, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio or halo$(C_1-C_6)$alkylthio, and wherein 4-cyclopropyl-1,2,3-thiadiazole-5-carboxylic acid and methyl 4-cyclopropyl-1,2,3-thiadiazole-5-carboxylate are excluded, and salts thereof.

(8) The plant disease control agent for agricultural and horticultural use for sterilizing seeds according to (7), wherein $R^1$, $R^2$, $R^3$, $R^4$ and $R^5$ are the same or different and each represents a hydrogen atom; a halogen atom; $(C_1-C_6)$alkyl; halo$(C_1-C_6)$alkyl; $(C_2-C_6)$alkenyl; halo$(C_2-C_6)$alkenyl; phenyl or substituted phenyl having from 1 to 5 substituents Z which are the same or different.

(9) A method of using a plant disease control agent for agricultural and horticultural use, which comprises treating a seed of an objective plant or a cultivation carrier for sowing an objective plant with an effective amount of the plant disease control agent for agricultural and horticultural use according to (7) or (8).

(10) The method of using a plant disease control agent for agricultural and horticultural use according to (9), wherein the seed of an objective plant is treated.

(11) The method of using a plant disease control agent for agricultural and horticultural use according to (10), wherein the effective amount is from 0.0001 to 40% by weight based on the weight of the seed of an objective plant.

(12) The method of using a plant disease control agent for agricultural and horticultural use according to (9), wherein the cultivation carrier for sowing an objective plant is treated.

(13) The method of using a plant disease control agent for agricultural and horticultural use according to (12), wherein the effective amount is from 0.0001 to 10% by weight based on the weight of the cultivation carrier for sowing an objective plant.

The present invention provides a plant disease control agent for agricultural and horticultural use which not only has excellent performance in comparison with the conventional art, particularly an excellent safety to objective plants and an excellent controlling effect but also has an extremely long-lasting effect, and provides a method of using the controlling agent with more efficiency.

BEST MODE FOR CARRYING OUT THE INVENTION

In the definition of formula (I) of 4-cyclopropyl-1,2,3-thiadiazole compounds of the invention, "a halogen atom" means a chlorine atom, a bromine atom, an iodine atom or a fluorine atom.

"$(C_1-C_6)$Alkyl" and "$(C_1-C_6)$alkyl" moiety mean linear or branched alkyl containing from 1 to 6 carbon atoms, such as methyl, ethyl, n-propyl, isopropyl, n-butyl, isobutyl, sec-butyl, t-butyl, n-pentyl, neopentyl and n-hexyl. Likewise, "$(C_1-C_{10})$alkyl" means linear or branched alkyl containing from 1 to 10 carbon atoms. Also, "$(C_1-C_{20})$alkyl" means linear or branched alkyl containing from 1 to 20 carbon atoms.

"Halo$(C_1-C_6)$alkyl" and "halo$(C_1-C_6)$alkyl" moiety mean linear or branched alkyl containing from 1 to 6 carbon atoms and substituted by 1 or more halogen atoms which are the same or different, and are examples thereof include trifluoromethyl, difluoromethyl, perfluoroethyl, perfluoroisopropyl, chloromethyl, bromomethyl, 1-bromoethyl, 2,3-dibromopropyl and the like. Likewise, "halo$(C_1-C_{10})$alkyl" means the above-described $(C_1-C_{10})$alkyl substituted by one or more halogen atoms which are the same or different.

"$(C_3-C_6)$Cycloalkyl" means alicyclic alkyl containing from 3 to 6 carbon atoms, such as cyclopropyl, cyclobutyl, cyclopentyl, cyclohexyl, 2-methylcyclopropyl and 2-methylcyclopentyl. Likewise, "$(C_3-C_{10})$cycloalkyl" means alicyclic alkyl containing from 3 to 10 carbon atoms. Also, "$(C_3-C_{12})$cycloalkyl" means alicyclic alkyl containing from 3 to 12 carbon atoms.

"Halo$(C_3-C_{12})$cycloalkyl" means the above-described $(C_3-C_{12})$cycloalkyl substituted with one or more halogen atoms which are the same or different.

"$(C_2-C_6)$Alkenyl" means linear or branched alkenyl containing from 2 to 6 carbon atoms and examples thereof include vinyl, allyl, 2-butenyl, 2-methyl-2-propenyl, 1-methyl-2-propenyl, 1-methyl-2-butenyl, 2-methyl-2-butenyl, 2-pentenyl, 2-hexenyl and the like. Likewise, "$(C_2-C_{10})$alkenyl" means linear or branched alkenyl containing from 2 to 10 carbon atoms. Also, "$(C_2-C_{20})$alkenyl" means linear or branched alkenyl containing from 2 to 20 carbon atoms.

"Halo$(C_2-C_6)$alkenyl" means the above-described $(C_2-C_6)$alkenyl substituted with one or more halogen atoms which are the same or different. Likewise, "halo$(C_2-C_{20})$alkenyl" means the above-described $(C_2-C_{20})$alkenyl substituted with one or more halogen atoms which are the same or different.

"$(C_2-C_{20})$Alkynyl" means linear or branched alkynyl containing from 2 to 20 carbon atoms and examples thereof include ethynyl, 2-propynyl, 2-butynyl, 1-methyl-2-propynyl and the like.

"Halo$(C_2-C_{20})$alkynyl" means the above-described $(C_2-C_{20})$alkynyl substituted with one or more halogen atoms which are the same or different.

"Aryl" means an aromatic group and examples thereof include phenyl, 1-naphthyl, 2-naphthyl and the like.

"$(C_2-C_6)$Alkylene" means linear or branched alkylene containing from 2 to carbon atoms and examples thereof include ethylene, trimethylene, tetramethylene, pentamethylene and the like.

"$(C_1-C_6)$Alkoxy" and "$(C_1-C_6)$alkoxy" moiety mean linear or branched alkoxy containing from 1 to 6 carbon atoms and examples thereof include methoxy, ethoxy, n-propoxy, isopropoxy, n-butoxy, sec-butoxy, t-butoxy, n-pentyloxy, isopentyloxy, neopentyloxy group, n-hexyloxy and the like.

"Halo$(C_1-C_6)$alkoxy" means linear or branched alkoxy containing from 1 to 6 carbon atoms substituted with one or more halogen atoms which are the same or different and examples thereof include difluoromethoxy, trifluoromethoxy, 2,2,2-trifluoroethoxy group and the like.

"$(C_1-C_6)$Alkoxycarbonyl" and "$(C_1-C_6)$alkoxycarbonyl" moiety mean linear or branched alkoxycarbonyl containing from 1 to 6 carbon atoms and examples thereof include methoxycarbonyl, ethoxycarbonyl, n-propoxycarbonyl, isopropoxycarbonyl, n-butoxycarbonyl, t-butoxycarbonyl and the like.

"$(C_1-C_6)$Alkylthio" and "$(C_1-C_6)$alkylthio" moiety mean linear or branched alkylthio containing from 1 to 6 carbon atoms and examples thereof include methylthio, ethylthio, n-propylthio, isopropylthio, n-butylthio, sec-butylthio, t-butylthio, n-pentylthio, isopentylthio, n-hexylthio and the like.

"Halo$(C_1-C_6)$alkylthio" means the above-described linear or branched $(C_1-C_6)$alkylthio substituted with one or more halogen atoms which are the same or different.

"$(C_1-C_6)$Alkylsulfinyl" means linear or branched alkylsulfinyl containing from 1 to 6 carbon atoms and examples thereof include methylsulfinyl, ethylsulfinyl, n-propylsulfinyl, isopropylsulfinyl, n-butylsulfinyl, sec-butylsulfinyl, t-butyl sulfinyl, n-pentylsulfinyl, isopentylsulfinyl, n-hexylsulfinyl and the like.

"Halo $(C_1-C_6)$alkylsulfinyl" means the above-described linear or branched $(C_1-C_6)$alkylsulfinyl substituted with one or more halogen atoms which are the same or different.

"$(C_1-C_6)$Alkylsulfonyl" and "$(C_1-C_6)$alkylsulfonyl" moiety mean linear or branched alkylsulfonyl containing from 1 to 6 carbon atoms and examples thereof include methylsulfonyl, ethylsulfonyl, n-propylsulfonyl, isopropylsulfonyl, n-butylsulfonyl, sec-butylsulfonyl, t-butylsulfonyl, n-pentylsulfonyl, isopentylsulfonyl, n-hexylsulfonyl and the like. Likewise, "$(C_1-C_{20})$alkylsulfonyl" means linear or branched alkylsulfonyl containing from 1 to 20 carbon atoms.

"Halo$(C_1-C_6)$alkylsulfonyl" means the above-described linear or branched $(C_1-C_6)$alkylsulfonyl substituted with one or more halogen atoms which are the same or different. Likewise, "halo$(C_1-C_{20})$ahlkylsulfonyl" means the above-described linear or branched $(C_1-C_{20})$alkylsulfonyl substituted with one or more halogen atoms which are the same or different.

"Heterocyclic ring" and "heterocyclic ring" moiety mean 5- or 6-membered heterocyclic ring containing one or more hetero atoms which are the same or different and are selected from an oxygen atom, a sulfur atom and a nitrogen atom. Examples of the heterocyclic ring include 5- or 6-membered heterocyclic rings and condensed heterocyclic rings such as thiazole, isothiazole, pyrazole, imidazole, oxazole, isoxazole, triazole, 1,2,3-thiadiazole, pyridine, pyrimidine, triazine, benzothiazole and quinoline.

Examples of salts of the 4-cyclopropyl-1,2,3-thiadiazole compounds of the invention represented by formula (I) include inorganic acid salts such as hydrochloride, sulfate, nitrate and phosphate; organic acid salts such as acetate, fumarate, maleate, oxalate, methanesulfonate, benzenesulfonate and p-toluenesulfonate; alkali metal salts such as lithium salt, sodium salt and potassium salt; alkaline earth metal salts such as magnesium salt and calcium salt; and salts with organic bases such as triethylamine, pyridine and 4-dimethylaminopyridine.

Some of the 4-cyclopropyl-1,2,3-thiadiazole compounds of the invention represented by formula (I) contain one or more asymmetric center, and also there is cases where two or more optical isomers and diastereomers exist. The invention includes all of respective optical isomers and mixtures containing them in any content. Also, with regard to some of the 4-cyclopropyl-1,2,3-thiadiazole compounds of the invention represented by formula (I), there exist two geometrical isomers due to a carbon-carbon double bond or carbon-nitrogen double bond in the structural formulae thereof. The invention includes all of the respective geometrical isomers and mixtures containing them in any content.

In the compounds of the invention represented by formula (I), $R^1$, $R^2$, $R^3$, $R^4$ and $R^5$ are preferably, which are the same or different, a hydrogen atom; a halogen atom; $(C_1-C_6)$alkyl; halo$(C_1-C_6)$alkyl; $(C_2-C_6)$alkenyl; halo$(C_2-C_6)$alkenyl; phenyl or substituted phenyl having 1 to 5 substituents Z which are the same or different. $R^1$ is more preferably a hydrogen atom, $(C_1-C_3)$alkyl or phenyl which are substituted with a halogen atom, and most preferably a hydrogen atom. $R^2$, $R^3$, $R^4$ and $R^5$ are more preferably, which are the same or different, a hydrogen atom or $(C_1-C_3)$alkyl, and most preferably a hydrogen atom.

$R^6$ is preferably —C(=W$^1$)YR$^7$,

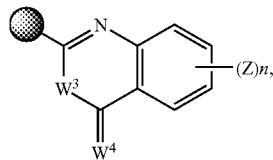

or cyano, and more preferably —C(=W$^1$)YR$^7$.

In the above formula, $R^7$ is preferably $(C_3-C_{20})$alkyl; halo$(C_3-C_{20})$alkyl; $(C_3-C_{20})$alkenyl; halo$(C_3-C_{20})$alkenyl; $(C_3-C_{20})$alkynyl; halo$(C_3-C_{20})$alkynyl; $(C_4-C_{12})$cycloalkyl; halo$(C_4-C_{12})$cycloalkyl; $(C_1-C_6)$alkoxy$(C_1-C_6)$alkyl; $(C_1-C_6)$alkylthio$(C_1-C_6)$alkyl; phenyl$(C_1-C_4)$alkyl which may be substituted on its ring with a substituent Z; phenyloxy$(C_1-C_4)$alkyl which may be substituted on its ring with a substituent Z; phenylthio$(C_1-C_4)$alkyl which may be substituted on its ring with a substituent Z; phenyl which may be substituted on its ring with a substituent Z; carboxy$(C_1-C_6)$alkyl; $(C_1-C_6)$alkoxycarbonyl$(C_1-C_6)$alkyl; carbamoyl$(C_1-C_6)$alkyl; carbamoyl$(C_1-C_6)$alkyl having on the nitrogen atom from 1 to 2 substituents which are the same or different and are selected from $(C_1-C_{10})$alkyl, halo$(C_1-C_{10})$alkyl, $(C_2-C_{10})$alkenyl, $(C_3-C_{10})$cycloalkyl, phenyl which may be substituted with a substituent Z and phenyl$(C_1-C_6)$alkyl which may be substituted on its ring with a substituent Z; cyano$(C_1-C_6)$alkyl; heterocyclic ring which may be substituted with a substituent Z; $(C_1-C_{20})$alkylsulfonyl; halo$(C_1-C_{20})$alkylsulfonyl; arylsulfonyl which may be substituted with a substituent Z, and —N=C(R$^8$)R$^9$ wherein R$^8$ and R$^9$ are preferably, which are the same or different, a hydrogen atom, $(C_1-C_6)$alkyl, halo$(C_1-C_6)$alkyl, $(C_3-C_6)$cycloalkyl or a phenyl group which may be substituted with a substituent Z, and more preferably $(C_8-C_{20})$alkyl, halo$(C_8-C_{20})$alkyl, thiazolyl or benzothiazolyl.

Y is preferably an oxygen atom, a sulfur atom, —NH— or —NHO—, and W$^1$ is preferably an oxygen atom or a sulfur atom.

Here, as a preferred combination of $R^1$, $R^2$, $R^3$, $R^4$, $R^5$ and $R^6$, $R^1$, $R^2$, $R^3$, $R^4$ and $R^5$ represent a hydrogen atom, and $R^6$ represents —C(=W$^1$)YR$^7$ wherein R$^7$ represents $(C_3-C_{10})$alkyl or substituted phenyl$(C_1-C_6)$alkyl having on its ring one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and $(C_1-C_6)$alkoxycarbonyl, and W$^1$ and Y represent an oxygen atom.

Also, preferred examples thereof include compounds wherein $R^1$, $R^2$, $R^3$, $R^4$ and $R^5$ represent a hydrogen atom, and $R^6$ represents —C(=W$^1$)YR$^7$ wherein R$^7$ represents $(C_1-C_6)$alkyl; substituted phenyl$(C_1-C_6)$alkyl having on its ring one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and $(C_1-C_6)$alkoxycarbonyl; substituted phenyl having one or more substituents which are the same or different and are selected from a halogen atom, cyano, methyl, ethyl, n-propyl, n-butyl, t-butyl, halo$(C_1-C_6)$alkyl, methoxy, ethoxy, halo$(C_1-C_6)$alkoxy and $(C_1-C_6)$alkoxycarbonyl; thiazolyl; substituted thiazolyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl, benzothiazolyl; substituted benzothiazolyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl; pyrimidyl; substituted pyrimidyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl; phenylsulfonyl or phenylsulfonyl having one or more substituents which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy and phenyl, W$^1$ represents an oxygen atom and Y represents —NH—.

Z's are preferably, which are the same or different, a halogen atom; cyano; nitro; $(C_1-C_6)$alkyl; halo$(C_1-C_6)$alkyl; $(C_3-C_{12})$cycloalkyl; halo$(C_3-C_{12})$cycloalkyl; phenyl optionally having substituents which are the same or different and are selected from a halogen atom, hydroxyl, cyano, nitro, $(C_1-C_6)$alkyl; a halo$(C_1-C_6)$alkyl group, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl and a substituted carbamoyl group having a substituent(s) X on the nitrogen atom; $(C_1-C_6)$alkoxy; halo$(C_1-C_6)$alkoxy; $(C_1-C_6)$alkylthio; halo$(C_1-C_6)$alkylthio; $(C_1-C_6)$alkylsulfinyl; halo$(C_1-C_6)$alkylsulfinyl; $(C_1-C_6)$alkylsulfonyl; halo$(C_1-C_6)$alkylsulfonyl; phenoxy which may have a substituent(s) which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$alkoxycarbonyl, carbamoyl X is preferably $(C_1-C_{10})$alkyl.

n is preferably an integer of from 0 to 3, and $W^3$ and $W^4$ are preferably an oxygen atom.

Although typical production processes of the present invention are schematically shown below, the present invention are not limited thereto.

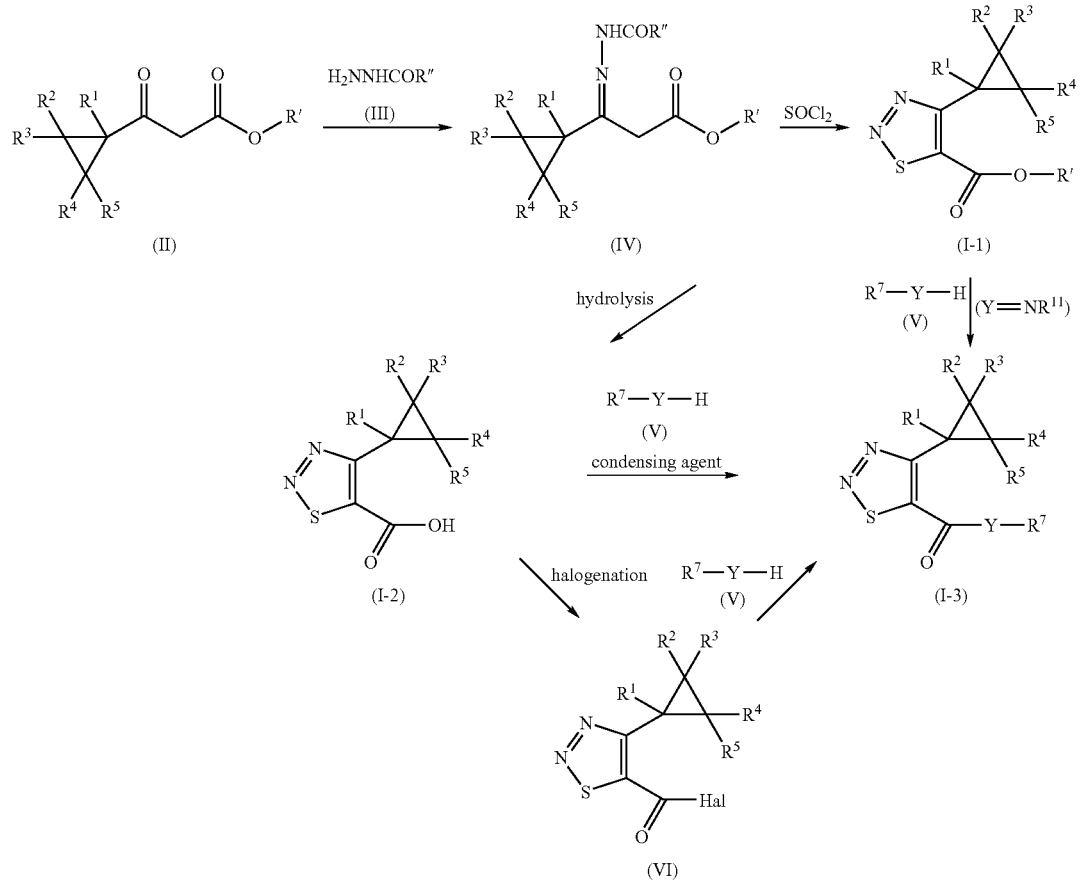

and substituted carbamoyl having a substituent(s) X on the nitrogen atom; phenyl$(C_1-C_3)$alkyloxy which may have a substituent(s) which are the same or different and are selected from a halogen atom, hydroxyl, cyano, nitro, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio, carboxyl, $(C_1-C_6)$ alkoxycarbonyl, carbamoyl and substituted carbamoyl having a substituent(s) X on the nitrogen atom; carboxyl; $(C_1-C_6)$alkoxycarbonyl; carbamoyl which may be substituted with a substituent(s) X or $(C_1-C_6)$alkylcarbonyl, and more preferably a halogen atom; cyano; $(C_1-C_6)$alkyl; halo$(C_1-C_6)$alkyl; phenyl which may have a substituent(s) which are the same or different and are selected from a halogen atom, cyano, $(C_1-C_6)$alkyl, halo$(C_1-C_6)$alkyl, $(C_1-C_6)$alkoxy, halo $(C_1-C_6)$alkoxy, $(C_1-C_6)$alkylthio, halo$(C_1-C_6)$alkylthio and $(C_1-C_6)$alkoxycarbonyl; $(C_1-C_6)$alkoxy; halo$(C_1-C_6)$alkoxy; $(C_1-C_6)$alkylthio; halo$(C_1-C_6)$alkylthio; phenoxy which may have a substituent(s) which are the same or different and are selected from a halogen atom, cyano, $(C_1-C_6)$alkyl, halo$(C_1-C_6)$alkyl, $(C_1-C_6)$alkoxy, halo$(C_1-C_6)$alkoxy, $(C_1-C_6)$alkylthio, halo$(C_1-C_6)$alkylthio and $(C_1-C_6)$alkoxycarbonyl.

In the above scheme, $R^1, R^2, R^3, R^4, R^5, R^7, R^{11}$ and Y have the same meanings as defined above, R' represents $(C_1-C_6)$ alkyl, R" represents $(C_1-C_6)$alkyl, $(C_1-C_6)$alkoxy or amino, and Hal represents a halogen atom.

A ketoester represented by formula (II) is allowed to react with a compound represented by formula (III) in the presence or absence of an inert solvent to give a hydrazone (IV), and the hydrazone (IV) is allowed to react with thionyl chloride with or without isolation and in the presence or absence of an inert solvent to give a 1,2,3-thiadiazole carboxylic acid ester compound of the invention represented by formula (I-1). The ester compound (I-1) is hydrolyzed with or without isolation and in the presence or absence of an inert solvent to prepare a 1,2, 3-thiadiazole carboxylic acid of the invention represented by formula (I-2), and the carboxylic acid (I-2) is allowed to react with a compound represented by formula (V), with or without isolation, in the presence or absence of an inert solvent and in the presence of a condensing agent to give a 1,2,3-thiadiazole compound of the invention represented by formula (I-3). The 1,2,3-thiadiazole compound of the invention represented by formula (I-3) can also be produced by halogenating the 1,2, 3-thiadiazole carboxylic acid compound of the invention represented by formula (I-2) in the presence or absence of an inert solvent to give a carboxylic acid halide represented by formula (VI), and reacting the carboxylic acid halide (VI) with a compound represented by formula (V) with or without isolation in the presence or absence of an inert solvent. When Y represents $NR^{11}$, the 1,2,3-thiadiazole compound of the invention represented by formula (I-3) can also be produced by reacting the 1,2,3-thiadiazole carboxylic acid ester compound of the invention represented by formula (I-1) with the compound represented by formula (V) in the presence or absence of an inert solvent.

1-1) Formula (II)→Formula (IV)

The starting substance of the ketoester represented by formula (II) can be produced by or according to the process described in known literature (e.g., *J. Org. Chem.*, 43, 2078 (1978)). Examples of the compound represented by formula (III) include, for example, hydrazides, semicarbazides and carbazic acid esters.

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran (THF) and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide, 1,3-dimethyl-2-imidazolinone, water and acetic acid. These inert solvents can be used alone or as a mixture of two or more thereof.

In this reaction, acids or bases can also be used. Examples of the acid to be used in this reaction include, for example, carboxylic acids such as formic acid, acetic acid and propionic acid; sulfonic acids such as methanesulfonic acid and p-toluenesulfonic acid, sulfuric acid and hydrochloric acid. Examples of the base include, for example, inorganic bases such as sodium hydroxide, potassium hydroxide, sodium acetate, potassium acetate, sodium carbonate, potassium carbonate, sodium hydrogencarbonate and potassium hydrogencarbonate; tertiary amines such as triethylamine, diisopropylethylamine and 1,8-diazabicyclo[5.4.0]undec-7-ene and nitrogen-containing aromatic compounds such as pyridine and dimethylaminopyridine. The amount of the acid or base to be used may properly be selected within the range of from 0.001 to 5 mols per mol of the compound represented by formula (II).

Since this reaction is an equimolar reaction, it is sufficient to use the compound represented by formula (III) in an amount equimolar to that of the ketoester represented by formula (II). However, it is possible to use either of the reactants in an excess amount. The reaction temperature is usually 0° C. to 150° C., and the reaction can be conducted at a temperature in the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound. After completion of the reaction, the desired compound can be used for the subsequent reaction without isolation.

1-2) Formula (IV)→Formula (I-1)

In this reaction, a solvent may or may not be used. As the solvent to be used in the invention, any solvent can be used so long as it does not seriously inhibit the reaction. Examples of the solvent include inert solvents such as chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide and 1,3-dimethyl-2-imidazolinone. These inert solvents can be used alone or as a mixture of two or more thereof.

The amount of thionyl chloride to be used in this reaction may properly be selected in the range of from an equimolar amount to a large excess amount based on the hydrazone represented by formula (IV). The reaction temperature is usually 0° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound. After completion of the reaction, the desired compound can be used for the subsequent reaction without isolation.

1-3) Formula (I-1)→Formula (I-2)

In this reaction, water is used as a solvent, and water may be used by mixing with other solvent. As the solvent to be mixed with water to use, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide and 1,3-dimethyl-2-imidazolinone. These inert solvents can be used alone or as a mixture of two or more thereof.

Examples of the base to be used in this reaction include, for example, inorganic bases such as sodium hydroxide, potassium hydroxide and lithium hydroxide. The amount of the base to be used in this reaction may properly be selected within the range of from 1 to 10 mols per mol of the 1,2,3-thiadiazole carboxylic acid ester represented by formula (I-1). The reaction temperature is usually from −20° C. to 100° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound. After completion of the reaction, the desired compound can be used for the subsequent reaction without isolation.

1-4) Formula (I-2)→Formula (I-3)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide, 1,3-dimethyl-2-imidazolinone and water. These inert solvents can be used alone or as a mixture of two or more thereof.

Examples of the condensing agent to be used in this reaction include, for example, carbodiimides such as 1,3-dicyclohexylcarbodiimide, 1,3-diisopropylcarbodiimide and 1-ethyl-3-(3'-dimethylaminopropyl)carbodiimide hydrochloride; N,N'-carbonyldiimidazole; 2-chloro-1-methylpyridinium iodide; diethylphosphorocyanidate; phosphoric acid dichloride phenyl ester; cyanuric chloride; isobutyl chloroformate; chlorosulfonyl isocyanate and trifluoroacetic acid anhydride. The amount of the condensing agent to be used may properly be selected within the range of from 1 to 5 mols per mol of the 1,2,3-thiadiazole carboxylic acid compound represented by formula (I-2).

Also, bases may also be used in this reaction. Examples of the base to be used in this reaction include tertiary amines such as triethylamine, diisopropylamine and 1,8-diazabicyclo[5.4.0]undec-7-ene and nitrogen-containing aromatic compounds such as pyridine and dimethylaminopyridine. The amount of the base to be used may properly be selected within the range of from 0.1 to 5 mols per mol of the 1,2,3-thiadiazole carboxylic acid compound represented by formula (I-2).

Since this reaction is an equimolar reaction, it is sufficient to use the compound represented by formula (V) in an amount equimolar to that of the 1,2,3-thiadiazole carboxylic acid compound represented by formula (I-2). However, it is possible to use either of the reactants in an excess amount. The reaction temperature is usually from −20° C. to 150° C., and the reaction can be conducted at a temperature in the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

1-5) Formula (I-2) to Formula (VI)

In this reaction, a solvent may or may not be used. As the solvent to be used in the invention, any solvent can be used so long as it does not seriously inhibit the reaction. Examples of the solvent include inert solvents such as chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide and 1,3-dimethyl-2-imidazolinone. These inert solvents can be used alone or as a mixture of two or more thereof.

Examples of the halogenating agent to be used in this reaction include thionyl chloride, phosphorus oxychloride, phosphorus oxybromide, phosphorus pentachloride and phosphorus pentabromide. The amount of the halogenating agent to be used may properly be selected within the range of from 1 to 10 mols per mol of the 1,2,3-thiadiazole carboxylic acid compound represented by formula (I-2). The reaction temperature is usually from −20° C. to 150° C., and the reaction can be conducted at a temperature in the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound. After completion of the reaction, the desired compound can be used for the next reaction without isolation.

1-6) Formula (VI)→Formula (I-3)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide, 1,3-dimethyl-2-imidazolinone and water. These inert solvents can be used alone or as a mixture of two or more thereof.

Examples of the base to be used in this reaction include inorganic bases such as sodium hydroxide, potassium hydroxide, sodium acetate, potassium acetate, sodium carbonate, potassium carbonate, sodium hydrogencarbonate and potassium hydrogencarbonate; tertiary amines such as triethylamine, diisopropylamine and 1,8-diazabicyclo[5.4.0]undec-7-ene and nitrogen-containing aromatic compounds such as pyridine and dimethylaminopyridine. The amount of the base to be used may properly be selected within the range of from 1 to 5 mols per mol of the compound represented by formula (VI).

Since this reaction is an equimolar reaction, it is sufficient to use the compound represented by formula (V) in an amount equimolar to that of the 1,2,3-thiadiazole carboxylic acid compound represented by formula (VI). However, it is possible to use either of the reactants in an excess amount. The reaction temperature is usually from −20° C. to 150° C., and the reaction can be conducted at a temperature in the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

1-7) Formula (I-1)→Formula (I-3)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide, 1,3-dimethyl-2-imidazolinone and water. These inert solvents can be used alone or as a mixture of two or more thereof.

Since this reaction is an equimolar reaction, it is sufficient to use the compound represented by formula (V) in an amount equimolar to that of the 1,2,3-thiadiazole carboxylic acid compound represented by formula (I-1). However, it is possible to use either of the reactants in an excess amount. The reaction temperature is usually from −20° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

Production process 2

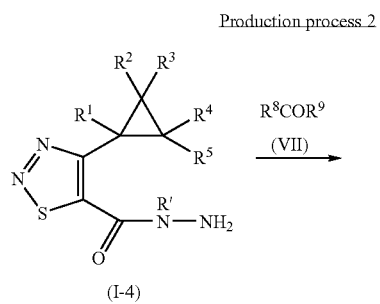

resented by formula (I-4) with a carbonyl compound represented by formula (VII). The 1,2,3-thiadiazole carbohydrazide compound represented by formula (I-4) can be produced according to the production process 1.

2-1) Formula (I-4)→Formula (I-5)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide, 1,3-dimethyl-2-imidazolinone, water and acetic acid. These inert solvents can be used alone or as a mixture of two or more thereof.

In this reaction, acids may be used and, examples of the acid to be used in this reaction include carboxylic acids such as formic acid, acetic acid and propionic acid; sulfonic acids such as methanesulfonic acid and p-toluenesulfonic acid; sulfuric acid and hydrochloric acid. The amount of the acid to be used may properly be selected within the range of from 0.001 to 5 mols per mol of the 1,2,3-thiadiazole carbohydrazide compound represented by formula (I-4).

Since this reaction is an equimolar reaction, it is sufficient to use the carbonyl compound represented by formula (VII) in an amount equimolar to that of the 1,2,3-thiadiazole carboxylic acid compound represented by formula (I-4). However, it is possible to use either of the reactants in an excess amount. The reaction temperature is usually from 0° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

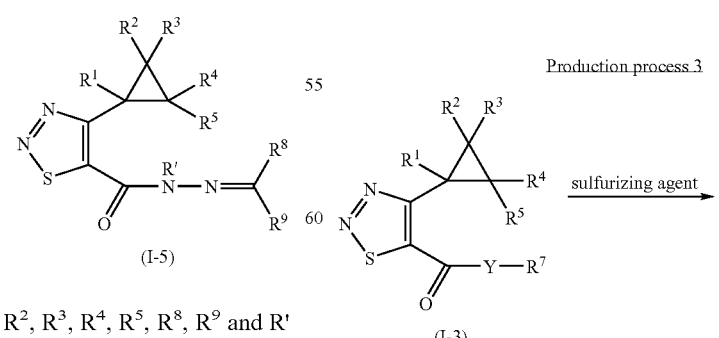

In the above formulae, $R^1$, $R^2$, $R^3$, $R^4$, $R^5$, $R^8$, $R^9$ and $R'$ have the same meanings as defined above. A 1,2,3-thiadiazole compound represented by formula (I-5) can be produced by reacting a 1,2,3-thiadiazole carbohydrazide compound rep-

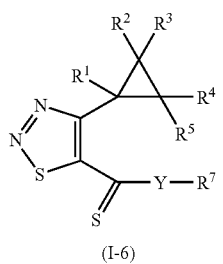

(I-6)

In the above formulae, $R^1, R^2, R^3, R^4, R^5, R^7$ and Y have the same meanings as defined above.

A 1,2,3-thiadiazole compound represented by formula (I-6) can be produced by reacting the 1,2,3-thiadiazole carbohydrazide compound represented by formula (I-3) with a sulfurizing agent.

3-1) Formula (I-3)→Formula (I-6)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitriles (e.g., acetonitrile), esters (e.g., ethyl acetate), amides (e.g., N,N-dimethylformamide and N,N-dimethylacetamide), dimethylsulfoxide, 1,3-dimethyl-2-imidazolinone, water and acetic acid. These inert solvents can be used alone or as a mixture of two or more thereof.

Examples of the sulfurizing agent to be used in this reaction include, for example, Lauesson's reagent and phosphorus pentasulfide.

The amount of the acid to be used may properly be selected within the range of from an equimolar amount to a large excess based on the 1,2,3-thiadiazole compound represented by formula (I-3). The reaction temperature is usually from 0° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

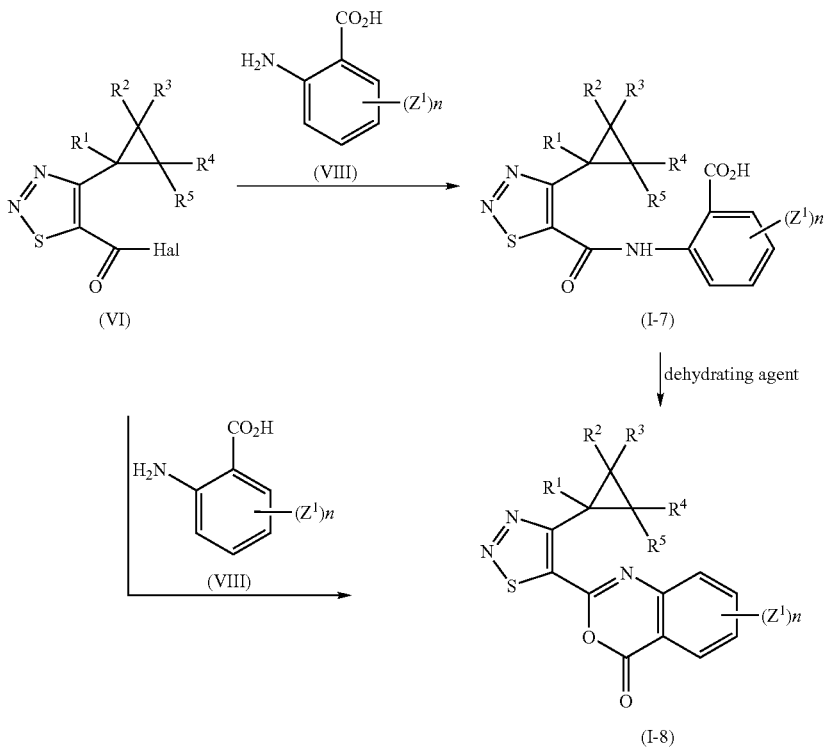

In the above formulae, $R^1, R^2, R^3, R^4, R^5$, Hal and n have the same meanings as defined above, and $Z^1$ has the same meaning as Z.

An oxazine compound represented by formula (I-8) can be produced by reacting the carboxylic acid halide represented by formula (VI) with an anthranilic acid represented by formula (VIII) in the presence or absence of an inert solvent to prepare a 1,2,3-thiadiazole carboxanilide represented by formula (I-7), isolating the carboxanilide compound (I-7), and then reacting it with a dehydrating agent in the presence or absence of an inert solvent. Also, the oxazine compound represented by formula (I-8) can also be directly produced by reacting the carboxylic acid halide represented by formula (VI) with the anthranilic acid represented by formula (VIII) in the presence or absence of an inert solvent.

4-1) Formula (VI)→Formula (I-7)

This reaction can be conducted according to the above 1-6).

After completion of the reaction, a desired compound is isolated from the reaction mixture containing the desired compound in a conventional manner and, if necessary, purified by recrystallization, distillation or column chromatography to thereby obtain the desired compound.

4-2) Formula (I-7)→Formula (I-8)

In this reaction, a solvent may or may not be used. As the solvent to be used in the invention, any solvent can be used so long as it does not seriously inhibit the reaction. Examples of the solvent include inert solvents such as alcohols (e.g., methanol, ethanol, propanol, butanol and 2-propanol), chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitriles (e.g., acetonitrile), esters (e.g., ethyl acetate), amides (e.g., N,N-dimethylformamide and N,N-dimethylacetamide), dimethylsulfoxide, 1,3-dimethyl-2-imidazolinone, water and acetic acid. These inert solvents can be used alone or as a mixture of two or more thereof.

Examples of the dehydrating agent to be used in this reaction include, for example, acid anhydrides such as trifluoroacetic acid anhydride and acetic acid anhydride; acid chlorides such as acetyl chloride, propionyl chloride, methyl chloroformate and isopropyl chloroformate; carbodiimides such as 1,3-dicyclohexylcarbodiimide, 1,3-diisopropylcarbodiimide and 1-ethyl-3-(3'-dimethylaminopropyl)carbodiimide hydrochloride; N,N'-carbonyldiimidazole; 2-chloro-1-methylpyridinium iodide; diethylphosphorocyanidate; phosphoric acid dichloride phenyl ester; cyanuric chloride; chlorosulfonyl isocyanate; thionyl chloride and phosphorus oxychloride. The amount of the condensing agent to be used may properly be selected within the range of from 1 to 5 mols per mol of the 1,2,3-thiadiazole carboxanilide compound represented by formula (I-7).

The reaction temperature is usually from 0° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

4-3) Formula (VI)→Formula (I-8)

In this reaction, the oxazine compound represented by formula (I-8) can directly be produced according to the above 4-1) by prolonging the reaction time.

Production process 5

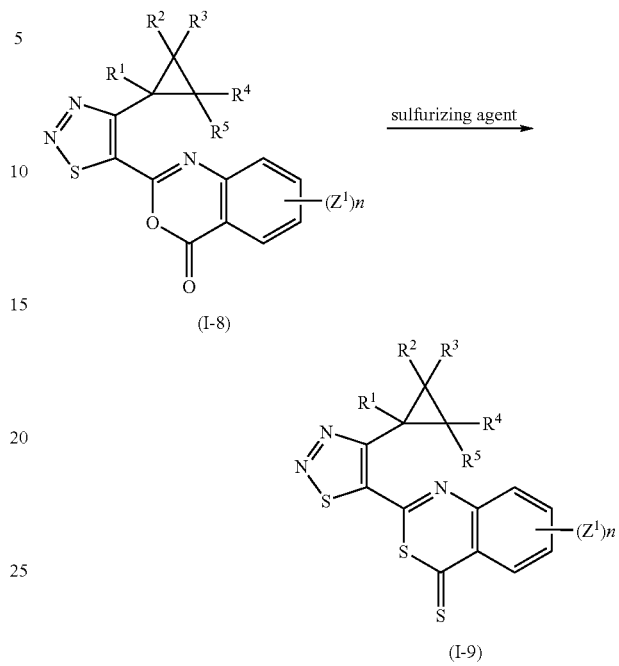

In the above formulae, $R^1$, $R^2$, $R^3$, $R^4$, $Z^1$ and n have the same meanings as defined above.

A thiazine compound represented by formula (I-9) can be produced by reacting the oxazine compound represented by formula (I-8) with a sulfurizing agent.

5-1) Formula (I-8)→Formula (I-9)

This reaction can be conducted according to the above 3-1).

After completion of the reaction, a desired compound is isolated from the reaction mixture containing the desired compound in a conventional manner and, if necessary, purified by recrystallization, distillation or column chromatography to thereby obtain the desired compound.

Production process 6

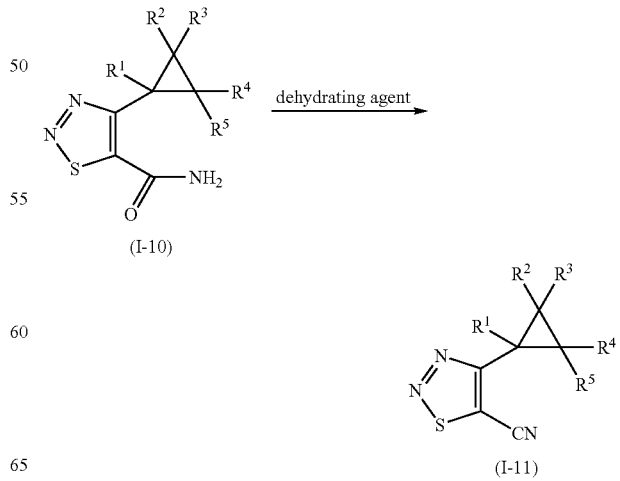

In the above formulae, $R^1$, $R^2$, $R^3$, $R^4$ and $R^5$ have the same meaning as defined above.

A 5-cyano-1,2,3-thiadiazole compound represented by formula (I-11) can be produced by reacting the 1,2,3-thiadiazole carboxamide compound represented by formula (I-10) with a dehydrating agent.

6-1) Formula (I-10)→Formula (I-11)

In this reaction, a solvent may or may not be used. As the solvent to be used in the invention, any solvent can be used so long as it does not seriously inhibit the reaction. Examples of the solvent include inert solvents such as chain or cyclic ethers (e.g., diethyl ether, tetrahydrofuran and dioxane), aromatic hydrocarbons (e.g., benzene, toluene and xylene), halogenated hydrocarbons (e.g., methylene chloride, chloroform and carbon tetrachloride), halogenated aromatic hydrocarbons (e.g., chlorobenzene and dichlorobenzene), nitrites (e.g., acetonitrile), esters (e.g., ethyl acetate), amides (e.g., N,N-dimethylformamide and N,N-dimethylacetamide), dimethylsulfoxide and 1,3-dimethyl-2-imidazolinone. These inert solvents can be used alone or as a mixture of two or more thereof.

Examples of the dehydrating agent to be used in this reaction include, for example, acid anhydrides such as acetic acid anhydride and trifluoroacetic acid anhydride; carbodiimides such as 1,3-dicyclohexylcarbodiimide and 1,3-diisopropylcarbodiimide; phosphorus oxychloride; phosphorus pentachloride and thionyl chloride. The amount of the dehydrating agent to be used may properly be selected within the range of an equimolar amount to a large excess amount based on the 1,2,3-thiadiazole carboxamide compound represented by formula (I-10). The reaction temperature is usually from 0° C. to 150° C., and the reaction can be conducted at a temperature within the range where the used inert solvent is refluxed. The reaction time varies depending upon the scale of the reaction and the reaction temperature, but may properly be selected from the range of from several minutes to 48 hours.

After completion of the reaction, a desired compound is isolated from the reaction mixture containing the desired compound in a conventional manner and, if necessary, purified by recrystallization, distillation or column chromatography to thereby obtain the desired compound.

Typical examples of the 4-cyclopropyl-1,2,3-thiadiazole compounds of the invention represented by formula (I) are illustrated in Tables 1 to 3 below. However, the invention is not limited thereto. Additionally, physical properties are shown in terms of melting point (° C.) or refractive index. Also, in Table 1, with regard to compounds appended by NMR as physical properties, $^1$H-NMR spectrum data thereof are shown in Table 4.

In the following tables, "Me" represents methyl, "Et" represents ethyl, "Pr" represents propyl, "Bu" represents butyl, "Ph" represents phenyl, "n-" represents normal, "i-" represents iso, "s-" represents secondary, "t-" represents tertiary, "c-" represents alicyclic hydrocarbon, and "*" applied to the compound No. means a salt of a compound designated by sign B.

Additionally, abbreviated signs represent the following compounds.

Q1:

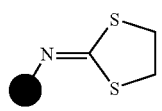

Q2:

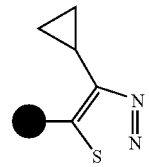

Q3:

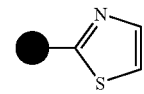

Q4:

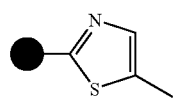

Q5:

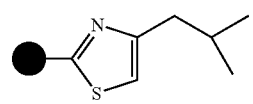

Q6:

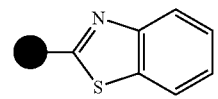

Q7:

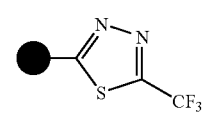

Q8:

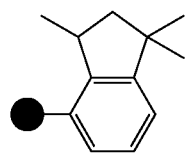

Q9:

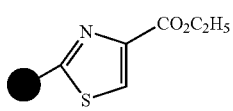

Q10:

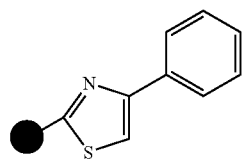

Q11:

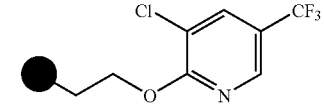

Q12:

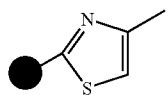

-continued
Q13: 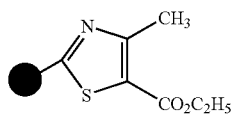
Q14: 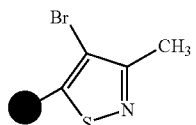
Q15: 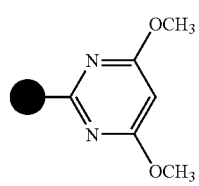
Q16: 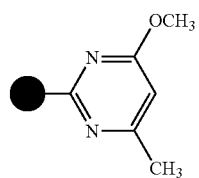
Q17: 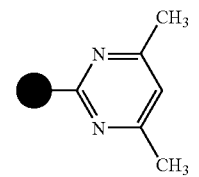
Q18: 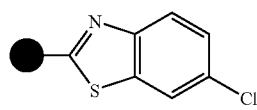
Q19: 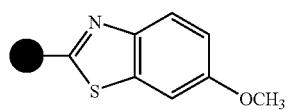
Q20: 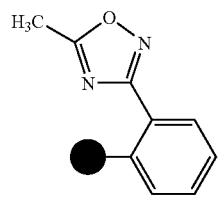
Q21: 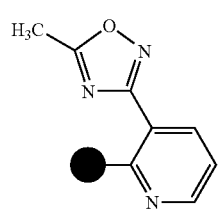
-continued
Q22: 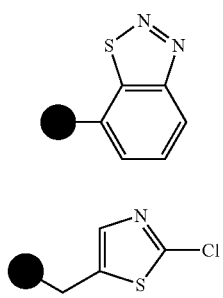
Q23: 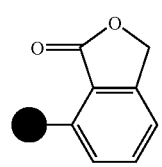
Q24: 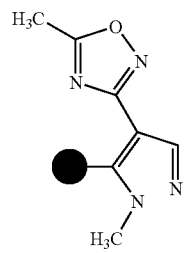
Q25: 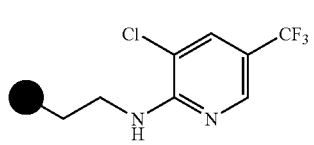
Q26: 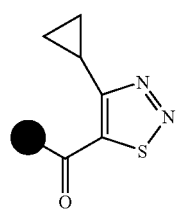
A: 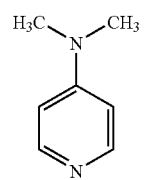
B: 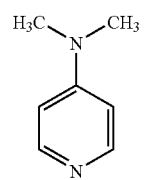

TABLE 1

Formula (I-1)

[Structure of Formula (I-1) showing a thiadiazole ring connected to a cyclopropyl group with substituents R1-R5, and a C(=W1)-Y-R7 group]

| No. | R1 | R2 | R3 | R4 | R5 | W1 | Y | R7 | melting point (° C.) or $n_D$ (° C.) |
|---|---|---|---|---|---|---|---|---|---|
| 1-1 | H | H | H | H | H | O | O | Et | 1.5304(22) |
| 1-2 | H | H | H | H | H | O | O | n-Pr | |
| 1-3 | H | H | H | H | H | O | O | i-Pr | |
| 1-4 | H | H | H | H | H | O | O | n-Bu | |
| 1-5 | H | H | H | H | H | O | O | i-Bu | |
| 1-6 | H | H | H | H | H | O | O | s-Bu | |
| 1-7 | H | H | H | H | H | O | O | t-Bu | |
| 1-8 | H | H | H | H | H | O | O | n-C$_8$H$_{17}$ | 1.5046(24) |
| 1-9 | H | H | H | H | H | O | O | CH$_2$Ph | 1.5749(24) |
| 1-10 | H | H | H | H | H | O | O | CH$_2$Ph(2-Cl) | 54 |
| 1-11 | H | H | H | H | H | O | O | CH$_2$Ph(3-Cl) | 1.5869(26) |
| 1-12 | H | H | H | H | H | O | O | CH$_2$Ph(4-Cl) | 75-76 |
| 1-13 | H | H | H | H | H | O | O | CH$_2$Ph(2-Me) | 72-73 |
| 1-14 | H | H | H | H | H | O | O | CH$_2$Ph(3-Me) | |
| 1-15 | H | H | H | H | H | O | O | CH$_2$Ph(4-Me) | 38 |
| 1-16 | H | H | H | H | H | O | O | CH$_2$Ph(2-OMe) | 64 |
| 1-17 | H | H | H | H | H | O | O | CH$_2$Ph(3-OMe) | |
| 1-18 | H | H | H | H | H | O | O | CH$_2$Ph(4-OMe) | 1.5746(26) |
| 1-19 | H | H | H | H | H | O | O | CH$_2$Ph(2-CN) | |
| 1-20 | H | H | H | H | H | O | O | CH$_2$Ph(3-CN) | |
| 1-21 | H | H | H | H | H | O | O | CH$_2$Ph(4-CN) | 109 |
| 1-22 | H | H | H | H | H | O | O | CH$_2$Ph(2-CO$_2$Me) | |
| 1-23 | H | H | H | H | H | O | O | CH$_2$Ph(3-CO$_2$Me) | |
| 1-24 | H | H | H | H | H | O | O | CH$_2$Ph(4-CO$_2$Me) | 61 |
| 1-25 | H | H | H | H | H | O | O | CH$_2$Ph(4-CO$_2$t-Bu) | 1.5496(23) |
| 1-26 | H | H | H | H | H | O | O | CH$_2$Ph(2,4-Cl$_2$) | |
| 1-27 | H | H | H | H | H | O | O | CH$_2$Ph(2,6-Cl$_2$) | |
| 1-28 | H | H | H | H | H | O | O | CH$_2$Ph(2,3-Cl$_2$) | |
| 1-29 | H | H | H | H | H | O | O | CH$_2$Ph(2,5-Cl$_2$) | |
| 1-30 | H | H | H | H | H | O | O | CH$_2$Ph(3,5-Cl$_2$) | 83-85 |
| 1-31 | H | H | H | H | H | O | O | CH$_2$Ph(3,4-Cl$_2$) | |
| 1-32 | H | H | H | H | H | O | O | CH$_2$Ph(2,4,6-Cl$_3$) | |
| 1-33 | H | H | H | H | H | O | O | CH$_2$Ph(2,4-Me$_2$) | |
| 1-34 | H | H | H | H | H | O | O | CH$_2$Ph(2,6-Me$_2$) | |
| 1-35 | H | H | H | H | H | O | O | CH$_2$Ph(3,5-Me$_2$) | |
| 1-36 | H | H | H | H | H | O | O | CH$_2$Ph(2,4,6-Me$_3$) | |
| 1-37 | H | H | H | H | H | O | O | CH$_2$Ph(2,4-(OMe)$_2$) | |
| 1-38 | H | H | H | H | H | O | O | CH$_2$Ph(2,6-(OMe)$_2$) | |
| 1-39 | H | H | H | H | H | O | O | CH$_2$Ph(3,5-(OMe)$_2$) | |
| 1-40 | H | H | H | H | H | O | O | CH$_2$Ph(2,4,6-(OMe)$_3$) | |
| 1-41 | H | H | H | H | H | O | O | CH(Me)Ph | 1.5615(26) |
| 1-42 | H | H | H | H | H | O | O | CH(Me)Ph(2-Cl) | |
| 1-43 | H | H | H | H | H | O | O | CH(Me)Ph(3-Cl) | |
| 1-44 | H | H | H | H | H | O | O | CH(Me)Ph(4-Cl) | 1.5754(24) |
| 1-45 | H | H | H | H | H | O | O | CH(Me)Ph(2-Me) | |
| 1-46 | H | H | H | H | H | O | O | CH(Me)Ph(3-Me) | |
| 1-47 | H | H | H | H | H | O | O | CH(Me)Ph(4-Me) | 1.5563(26) |
| 1-48 | H | H | H | H | H | O | O | CH(Me)Ph(2-OMe) | |
| 1-49 | H | H | H | H | H | O | O | CH(Me)Ph(3-OMe) | |
| 1-50 | H | H | H | H | H | O | O | CH(Me)Ph(4-OMe) | 1.5640(26) |
| 1-51 | H | H | H | H | H | O | O | Q1 | 107 |
| 1-52 | H | H | H | H | H | O | NH | H | 163 |
| 1-53 | H | H | H | H | H | O | NH | CH$_2$Ph | 97.5 |
| 1-54 | H | H | H | H | H | O | NH | CH$_2$Ph(2-Cl) | |
| 1-55 | H | H | H | H | H | O | NH | CH$_2$Ph(3-Cl) | |
| 1-56 | H | H | H | H | H | O | NH | CH$_2$Ph(4-Cl) | 118-120 |
| 1-57 | H | H | H | H | H | O | NH | CH$_2$Ph(2-Me) | |
| 1-58 | H | H | H | H | H | O | NH | CH$_2$Ph(3-Me) | |
| 1-59 | H | H | H | H | H | O | NH | CH$_2$Ph(4-Me) | 99-100 |
| 1-60 | H | H | H | H | H | O | NH | CH$_2$Ph(2-OMe) | |
| 1-61 | H | H | H | H | H | O | NH | CH$_2$Ph(3-OMe) | |

TABLE 1-continued

Formula (I-1)

$$\text{(I-1)}$$

| No. | R¹ | R² | R³ | R⁴ | R⁵ | W¹ | Y | R⁷ | melting point (° C.) or n_D (° C.) |
|---|---|---|---|---|---|---|---|---|---|
| 1-62 | H | H | H | H | H | O | NH | CH₂Ph(4-OMe) | 92-93 |
| 1-63 | H | H | H | H | H | O | NH | CH₂Ph(4-t-Bu) | 1.5642(25) |
| 1-64 | H | H | H | H | H | O | NH | CH₂Ph(4-CO₂Me) | |
| 1-65 | H | H | H | H | H | O | NH | CH₂Ph(4-OPh(4-Me)) | 1.5780(21) |
| 1-66 | H | H | H | H | H | O | NH | CH₂Ph(4-OPh(4-CF₃)) | 89-91 |
| 1-67 | H | H | H | H | H | O | NH | CH₂Ph(4-CO₂Me) | 102 |
| 1-68 | H | H | H | H | H | O | NH | CH₂Ph(4-OCH₂CF₃) | 105 |
| 1-69 | H | H | H | H | H | O | NH | CH₂Ph(2,4-(OMe)₂) | 126.9-127.5 |
| 1-70 | H | H | H | H | H | O | NH | CH(Me)Ph | 109 |
| 1-71 | H | H | H | H | H | O | NH | CH(Me)Ph(2-Cl) | |
| 1-72 | H | H | H | H | H | O | NH | CH(Me)Ph(3-Cl) | |
| 1-73 | H | H | H | H | H | O | NH | CH(Me)Ph(4-Cl) | 1.5976(20) |
| 1-74 | H | H | H | H | H | O | NH | CH(Me)Ph(2-Me) | |
| 1-75 | H | H | H | H | H | O | NH | CH(Me)Ph(3-Me) | |
| 1-76 | H | H | H | H | H | O | NH | CH(Me)Ph(4-Me) | |
| 1-77 | H | H | H | H | H | O | NH | CH(Me)Ph(2-OMe) | |
| 1-78 | H | H | H | H | H | O | NH | CH(Me)Ph(3-OMe) | |
| 1-79 | H | H | H | H | H | O | NH | CH(Me)Ph(4-OMe) | |
| 1-80 | H | H | H | H | H | O | NH | CH₂CH₂Ph | 1.5838(21) |
| 1-81 | H | H | H | H | H | O | NH | CH₂CH₂Ph(2,4-(OMe)₂) | 71 |
| 1-82 | H | H | H | H | H | O | NMe | CH₂Ph | 1.5899(24) |
| 1-83 | H | H | H | H | H | O | NMe | CH₂Ph(2-Cl) | |
| 1-84 | H | H | H | H | H | O | NMe | CH₂Ph(3-Cl) | |
| 1-85 | H | H | H | H | H | O | NMe | CH₂Ph(4-Cl) | |
| 1-86 | H | H | H | H | H | O | NMe | CH₂Ph(2-Me) | |
| 1-87 | H | H | H | H | H | O | NMe | CH₂Ph(3-Me) | |
| 1-88 | H | H | H | H | H | O | NMe | CH₂Ph(4-Me) | |
| 1-89 | H | H | H | H | H | O | NMe | CH₂Ph(2-OMe) | |
| 1-90 | H | H | H | H | H | O | NMe | CH₂Ph(3-OMe) | |
| 1-91 | H | H | H | H | H | O | NMe | CH₂Ph(4-OMe) | |
| 1-92 | H | H | H | H | H | O | NH | Ph | 139 |
| 1-93 | H | H | H | H | H | O | NH | Ph(3-i-Pr) | NMR |
| 1-94 | H | H | H | H | H | O | NH | Ph(3-O-i-Pr) | NMR |
| 1-95 | H | H | H | H | H | O | NH | Ph(3-Cl-4-Me) | 150-153 |
| 1-96 | H | H | H | H | H | O | NH | Ph(2,4-(OMe)₂) | 108-110 |
| 1-97 | H | H | H | H | H | O | NH | Ph(3,4-(OMe)₂) | 138 |
| 1-98 | H | H | H | H | H | O | NH | Ph(2-CO₂H) | NMR |
| 1-99 | H | H | H | H | H | O | NH | Ph(2-CO₂Me) | 104-105 |
| 1-100 | H | H | H | H | H | O | NH | Ph(2-CN) | 124 |
| 1-101 | H | H | H | H | H | O | NH | Ph(4-CH(Me)Et) | 125-126 |
| 1-102 | H | H | H | H | H | O | NH | Ph(3-O-i-Pr-4-CH(CF₃)₂) | 165-170 |
| 1-103 | H | H | H | H | H | O | NH | Ph(3-O-i-Pr-4-C(OMe)(CF₃)₂) | 136-141 |
| 1-104 | H | H | H | H | H | O | NH | Ph(2-(1,3-Me₂-Bu)-4-CH(CF₃)₂) | 1.5117(25) |
| 1-105 | H | H | H | H | H | O | NMe | Ph(2,4-(OMe)₂) | 90 |
| 1-106 | H | H | H | H | H | O | NMe | Ph(2-CO₂Me) | 1.5855(24) |
| 1-107 | H | H | H | H | H | O | NPh(2-CN) | CO-Q2 | 177-178 |
| 1-108 | H | H | H | H | H | O | NH | Q3 | 174-175 |
| 1-109 | H | H | H | H | H | O | NH | Q4 | 205-207 |
| 1-110 | H | H | H | H | H | O | NH | Q5 | 136-138 |
| 1-111 | H | H | H | H | H | O | NH | Q6 | 230 |
| 1-112 | H | H | H | H | H | O | NH | Q7 | 200(decomposition) |
| 1-113 | H | H | H | H | H | O | NH | OCH₂Ph | 1.5757(26) |
| 1-114 | H | H | H | H | H | O | NH | OCH₂Ph(4-Cl) | 89-90 |
| 1-115 | H | H | H | H | H | O | NH | NH₂ | NMR |
| 1-116 | H | H | H | H | H | O | NMe | NH₂ | NMR |
| 1-117 | H | H | H | H | H | O | NH | N=CHPh | 230-239 |
| 1-118 | H | H | H | H | H | O | NMe | N=CHPh | 159.0-160.5 |
| 1-119 | H | H | H | H | H | O | NH | NC=C(Me)Ph | 221-224 |
| 1-120 | H | H | H | H | H | O | NH | SO₂Me | 179-181 |
| 1-121 | H | H | H | H | H | O | NH | SO₂Ph | 211-212 |
| 1-122 | H | H | H | H | H | O | NH | SO₂CF₃ | 50-54 |

TABLE 1-continued

Formula (I-1)

(I-1)

| No. | R$^1$ | R$^2$ | R$^3$ | R$^4$ | R$^5$ | W$^1$ | Y | R$^7$ | melting point (° C.) or n$_D$ (° C.) |
|---|---|---|---|---|---|---|---|---|---|
| 1-123 | H | Me | H | H | H | O | O | H | |
| 1-124 | H | Me | H | H | H | O | O | OMe | NMR |
| 1-125 | H | Me | H | H | H | O | O | CH$_2$Ph | 1.5676(25) |
| 1-126 | H | Me | H | H | H | O | O | CH$_2$Ph(4-Cl) | 1.5691(26) |
| 1-127 | H | Me | H | H | H | O | NH | Ph(2,4-(OMe)$_2$) | 82.5-84.0 |
| 1-128 | Ph(4-Cl) | H | H | H | H | O | O | H | 158-160 |
| 1-129 | Ph(4-Cl) | H | H | H | H | O | O | OMe | 1.5731(26) |
| 1-130 | Ph(4-Cl) | H | H | H | H | O | O | CH$_2$Ph | 106.5-110.0 |
| 1-131 | Ph(4-Cl) | H | H | H | H | O | O | CH$_2$Ph(4-Cl) | 53.5-55.5 |
| 1-132 | Ph(4-Cl) | H | H | H | H | O | NH | Ph(2,4-(OMe)$_2$) | 163-164 |
| 1-133 | Me | H | H | H | H | O | O | H | |
| 1-134 | Me | H | H | H | H | O | O | OMe | NMR |
| 1-135 | Me | H | H | H | H | O | O | CH$_2$Ph | |
| 1-136 | Me | H | H | H | H | O | O | CH$_2$Ph(4-Cl) | |
| 1-137 | Me | H | H | H | H | O | NH | Ph(2,4-(OMe)$_2$) | 111-112 |
| 1-138 | H | Me | Me | Me | Me | O | O | H | NMR |
| 1-139 | H | Me | Me | Me | Me | O | O | OMe | NMR |
| 1-140 | H | Me | Me | Me | Me | O | O | CH$_2$Ph | 1.5390(21) |
| 1-141 | H | Me | Me | Me | Me | O | O | CH$_2$Ph(4-Cl) | paste |
| 1-142 | H | Me | Me | Me | Me | O | NH | Ph(2,4-(OMe)$_2$) | 155-158 |
| 1-143 | H | H | H | H | H | S | NH | Ph(3-Cl-4-Me) | 1.6698(22) |
| 1-144 | H | H | H | H | H | S | NH | Ph(2,4-(OMe)$_2$) | 113-114 |
| 1-145 | H | H | H | H | H | O | NH | CH$_2$CH=CH$_2$ | 78.1-78.7 |
| 1-146 | H | H | H | H | H | O | NH | CH$_2$C≡CH | 100.3-101.8 |
| 1-147 | H | H | H | H | H | O | NH | C(C$_2$H$_5$)$_2$C≡CH | 83.5-84.2 |
| 1-148 | H | H | H | H | H | O | NH | CH$_2$CH$_2$CH$_2$Cl | 78-80.3 |
| 1-149 | H | H | H | H | H | O | NH | Q8 | amorphous |
| 1-150 | H | H | H | H | H | O | NH | Ph(2-Ph(4-Cl)) | 184-185 |
| 1-151 | H | H | H | H | H | O | NH | Ph(2,6-Me$_2$) | 155-158 |
| 1-152 | H | H | H | H | H | O | NH | Ph(2,6-Et$_2$) | 108-109 |
| 1-153 | H | H | H | H | H | O | N-A | Ph(2,6-Me$_2$) | 131-132 |
| 1-154 | H | H | H | H | H | O | N-A | Ph(2,6-Et$_2$) | 111-112.6 |
| 1-155 | H | H | H | H | H | O | NH | Ph(2,5-(OMe)$_2$) | 119.5-120 |
| 1-156 | H | H | H | H | H | O | NH | Ph(2-Me)(4-OMe) | 102-103 |
| 1-157 | H | H | H | H | H | O | NH | SO$_2$Ph(4-Cl) | 143.3-147.2 |
| 1-158 | H | H | H | H | H | O | NH | SO$_2$Ph(2-Cl) | 132-137 |
| 1-159 | H | H | H | H | H | O | NH | SO$_2$NMe$_2$ | 148.5-150.5 |
| 1-160 | H | H | H | H | H | O | NH | CH(CN)Ph | 130.7-133.5 |
| 1-161 | H | H | H | H | H | O | NH | C(Me)$_2$Ph | 151-152 |
| 1-162 | H | H | H | H | H | O | NH | CH$_2$Ph(2,4-Me$_2$) | 115.9-116.3 |
| 1-163 | H | H | H | H | H | O | NH | CH$_2$Ph(2,5-Me$_2$) | 127.6-128.1 |
| 1-164 | H | H | H | H | H | O | NH | CH$_2$Ph(2,4-Cl$_2$) | 125.8-126.4 |
| 1-165 | H | H | H | H | H | O | NH | CH$_2$Ph(2,3-(OMe)$_2$) | 94.8-96 |
| 1-166 | H | H | H | H | H | O | NH | CH$_2$Ph(3,4-(OMe)$_2$) | 93.6-94.4 |
| 1-167 | H | H | H | H | H | O | NH | CH$_2$Ph(2,5-(OMe)$_2$) | 118.8-119.8 |
| 1-168 | H | H | H | H | H | O | NH | CH$_2$Ph(3,5-(OMe)$_2$) | 91.5-94 |
| 1-169 | H | H | H | H | H | O | NH | Q9 | 154.2-156.5 |
| 1-170 | H | H | H | H | H | O | NH | Q10 | 200.2-204.3 |
| 1-171 | H | H | H | H | H | O | NH | Q11 | 126.1-126.9 |
| 1-172 | H | H | H | H | H | O | NH | Q12 | 180.3-181.8 |
| 1-173 | H | H | H | H | H | O | NH | Q13 | 169.1-171.2 |
| 1-174 | H | H | H | H | H | O | NH | Q14 | 132.4-132.6 |
| 1-175 | H | H | H | H | H | O | NH | Q15 | 115.6-117.9 |
| 1-176 | H | H | H | H | H | O | NH | Q16 | 134.9-135.4 |
| 1-177 | H | H | H | H | H | O | NH | Q17 | 144.3-144.8 |

TABLE 1-continued

Formula (I-1)

$$\text{(I-1)}$$

| No. | R¹ | R² | R³ | R⁴ | R⁵ | W¹ | Y | R⁷ | melting point (° C.) or $n_D$ (° C.) |
|---|---|---|---|---|---|---|---|---|---|
| 1-178 | H | H | H | H | H | O | NH | Q18 | 219-222 |
| 1-179* | H | H | H | H | H | O | NH | Q18 | 207.1-208 |
| 1-180 | H | H | H | H | H | O | NH | Q19 | 198-199 |
| 1-181* | H | H | H | H | H | O | NH | Q19 | 170.8-173.4 |
| 1-182 | H | H | H | H | H | O | NH | Q20 | 128.5-129.5 |
| 1-183 | H | H | H | H | H | O | NH | Q21 | 147.5-149 |
| 1-184 | H | H | H | H | H | O | NH | Q22 | 162-164 |
| 1-185 | H | H | H | H | H | O | NH | Q23 | amorphous |
| 1-186 | H | H | H | H | H | O | NH | Q24 | 161-162 |
| 1-187 | H | H | H | H | H | O | NH | Q25 | 156.5-158 |
| 1-188 | H | H | H | H | H | O | O | Q26 | 92.2-92.9 |
| 1-189 | H | H | H | H | H | O | NH | Ph(2-CONHMe) | |
| 1-190 | H | H | H | H | H | O | NH | Ph(2-SMe) | |
| 1-191 | H | H | H | H | H | O | NH | Ph(2-SMe-5-CF₃) | |
| 1-192 | H | H | H | H | H | O | NH | Ph(2-SO₂Me) | 153.5-154.5 |
| 1-193 | H | H | H | H | H | O | S | Ph | |
| 1-194 | H | H | H | H | H | O | S | Ph(2-CN) | |
| 1-195 | H | H | H | H | H | O | S | Ph(2-CO₂Me) | |
| 1-196 | H | H | H | H | H | O | S | Ph(2-Cl) | |
| 1-197 | H | H | H | H | H | O | S | Ph(2,4-(OMe)₂) | |
| 1-198 | H | H | H | H | H | O | NH | SO₂Ph(2-CO₂Me) | 119.2-119.4 |
| 1-199 | H | H | H | H | H | O | NH | SO₂Ph(2-CO₂H) | 184-185 |
| 1-200 | H | H | H | H | H | O | NH | SO₂Ph(2-CONHMe) | 159.5-162.5 |
| 1-201 | H | H | H | H | H | O | NH | SO₂Ph(2-CN) | |
| 1-202 | H | H | H | H | H | O | NH | SO₂Ph(2-NO₂) | |
| 1-203 | H | H | H | H | H | O | NH | SO₂Ph(2-CF₃) | |
| 1-204 | H | H | H | H | H | O | NH | SO₂Ph(2-CF₃-4-Cl) | |
| 1-205 | H | H | H | H | H | O | NH | SO₂Ph(4-CF₃) | |
| 1-206 | H | H | H | H | H | O | NH | SO₂Ph(4-Me) | |

TABLE 2

Formula (I-8)

(I-8)

| No. | R¹ | R² | R³ | R⁴ | R⁵ | (Z¹)n | melting point (° C.) |
|---|---|---|---|---|---|---|---|
| 2-1 | H | H | H | H | H | H | 164-165 |

TABLE 3

Formula (I-11)

(I-11)

| No. | R¹ | R² | R³ | R⁴ | R⁵ | $n_D$ (° C.) |
|---|---|---|---|---|---|---|
| 3-1 | H | H | H | H | H | 1.5716(26) |

TABLE 4

| Compound No. | ¹H-NMR(TMS, δ value ppm), (solvent) |
|---|---|
| 1-93 | 1.20-1.40 (m, 10H), 2.5 (m, 1H), 2.89 (m, 1H), 7.05-7.50 (m, 4H), 8.30 (br.s, 1H) (solvent: CDCl₃) |

TABLE 4-continued

| Compound No. | $^1$H-NMR(TMS, δ value ppm), (solvent) |
|---|---|
| 1-94 | 1.20-1.40 (m, 10H), 2.5 (m, 1H), 4.55 (m, 1H), 6.72 (dd, 1H), 7.0-7.30 (m.3H), 8.30 (br.s, 1H) (solvent: CDCl$_3$) |
| 1-98 | 1.2-1.35 (m, 4H), 2.7-2.9 (m, 1H), 7.30 (m, 2H), 7.70 (t, 1H), 8.05 (d, 1H), 8.46 (d, 1H), 11.95 (br, 1H) (solvent: DMSO-d$_6$) |
| 1-115 | 1.12-1.30 (m, 4H), 3.30-3.45 (m, 1H), 4.73-5.25 (br, 2H), 9.42-10.04 (br, 1H) (solvent: DMSO-d$_6$) |
| 1-116 | 1.16-1.30 (m, 4H), 3.20-3.35 (m, 1H), 3.38 (s, 3H), 4.24 (br, 2H) (solvent: DMSO-d$_6$) |
| 1-124 | 1.07-1.09 (m, 1H), 1.28 (d, 3H), 1.58 (m, 1H), 1.78 (m, 1H), 2.66 (m, 1H) 3.96 (s, 3H) (solvent: CDCl$_3$) |
| 1-134 | 1.12 (m, 2H), 1.34 (m, 2H), 1.56 (s, 3H), 3.94 (s, 3H) (solvent: CDCl$_3$) |
| 1-138 | 1.19 (s, 6H), 1.36 (s, 6H), 2.19 (s, 1H) (solvent: CDCl$_3$) |
| 1-139 | 1.16 (s, 6H), 1.36 (s, 6H), 2.18 (s, 1H), 3.94 (s, 3H) (solvent: CDCl$_3$) |

The plant disease control agent for agricultural and horticultural use to be used in the invention contains the 4-cyclopropyl-1,2,3-thiadiazole compound represented by formula (I) or a salt thereof. In addition to the independent use, the compound can be used as a mixture with various compounds such as the compounds having a fungicidal activity described below, or can be applied together with them.

Examples of the compounds having a fungicidal activity include various fungicides such as melanine synthesis inhibitors, strobilurin series fungicides, ergosterol biosynthesis inhibitors, acid amide series fungicides, succinic acid synthesizing enzyme-inhibiting fungicides, acylalanine series fungicides, dicarboximide series fungicides, benzimidazole series fungicides, dithiocarbamate series fungicides, metal-containing fungicides and antibiotics.

As objects to which the plant disease control agent for agricultural and horticultural use containing the 4-cyclopropyl-1,2,3-thiadiazole compound represented by formula (I) or a salt thereof to be used for the method of use of the invention is applied, the following plant diseases are illustrated.

Such plant diseases are roughly classified into diseases caused by fungal, diseases caused by bacteria and plant diseases caused by virus, and include diseases caused by *Fungi Imperfecti* (e.g., disease caused by *Botrytis* sp., *Helminthosporium* sp., *Fusarium* sp., *Septoria* sp., *Cercospora* sp., *Pseudocercosporella* sp., *Rhynchosporium* sp., *Pyricularia* sp. or *Alternaria* sp.), diseases caused by *Basidiomycetes* (e.g., disease caused by *Hemileia* sp., *Rhizoctonia* sp., *Ustilago* sp., *Typhula* sp. or *Puccinia* sp.), diseases caused by *Ascomycetes* (e.g., disease caused by *Venturia* sp., *Podosphaera* sp., *Leptosphaeria* sp., *Blumeria* sp., *Erysiphe* sp., *Microdochium* sp., *Scierotinia* sp., *Gaeumannomyces* sp., *Monilinia* sp. or *Unsinula* sp.), diseases caused by other fungi (e.g., disease caused by *Ascochyta* sp., *Phoma* sp., *Pythium* sp., *Corticium* sp. or *Pyrenophora* sp.), diseases caused by bacteria (e.g., disease caused by *Pseudomonas* sp., *Xanthomonas* sp. or *Erwinia* sp.), diseases caused by viruses (e.g., tobacco mosaic virus) and the like.

As to individual diseases, the plant disease control agent for agricultural and horticultural use shows remarkable control effects on diseases, for example, disease of rice caused by *Pyricularia oryzae, Rhizoctonia solani, Cochibolus miyabeanus, Rhizopus chinensis, Pythium graminicola, Fusarium graminicola, Fusarium roseum, Mucor* sp., *Phoma* sp., *Tricoderma* sp. or *Gibberella fujikuroi*, disease of barley and wheat caused by *Blumeria graminis*, disease of cucumber caused by *Sphaerotheca fuliginea*, disease of eggplant caused by *Erysiphe cichoracoarum*, powdery mildew of other host plants, disease of barley and wheat caused by *Pseudocercosporella herpotrichoides*, disease of wheat caused by *Urocystis tritici*, disease of barley and wheat caused by *Microdochium nivalis, Pythium iwayamai, Typhlaishikariensis, Typhla* incarnate or *Sclerotinia borealis*, disease of barley and wheat caused by *Fusarium graminearum, Fusarium avenaceum, Fusarium culmorum* or *Microdochium nivalis*, rust of barley and wheat caused by *Puccinia recondite, Puccinia striiformis* or *Puccinia graminis*, damping-off of barley and wheat caused by *Gaeumannomyces graminis*, disease of oats caused by *Puccinia coronata*, rust of other plants, disease of cucumber and strawberry caused by *Botrytis cinerea*, disease of tomato and cabbage caused by *Sclerotinia sclerotiorum*, late blight of potato and tomato caused by *Phytophthora infestans*, late blight of other plants, downy mildew of cucumber caused by *Pseudoperonospora cubensis*, downy mildew of grape caused by *Plasmopara viticola*, downy mildew of various other plants, disease of apple caused by *Venturia inaequalis*, disease of apple caused by *Alternaria mali*, disease of pear caused by *Alternaria kikuchiana*, disease of citrus caused by *Diaporthe citri*, disease of citrus caused by *Elsinoe fawcetti*, disease of sugar beet caused by *Cercospora beticola*, disease of peanut caused by *Cerospora arachidicola*, disease of peanut caused by *Cercospora personata*, disease of wheat caused by *Septoria tritici*, disease of wheat caused by *Leptosphaeria nodorum*, disease of barley caused by *Pyrenophora teres*, disease of barley caused by *Pyrenophora graminea*, disease of barley caused by *Rhynchosporium secalis*, disease of wheat caused by *Ustilago nuda*, disease of wheat caused by *Tilletia caries*, disease of turf caused by *Rhizoctonia solani*, disease of turf caused by *Sclerotinia homoeocarpa*, diseases caused by *Pseutomonas* sp. (e.g., disease of cucumber caused by *Pseudomonas syringae* pv. *lachrymans*, disease of tomato caused by *Pseudomonas solanacearum* and disease of rice caused by *Pseudomonas glumae*), diseases caused by *Xanthomonas* sp. (e.g., disease of cabbage caused by *Xanthomonas campestris*, disease of rice caused by *Xanthomonas oryzae* and disease of citrus caused by *Xanthomonas citri*) and diseases caused by *Erwinia* sp. (e.g., disease of cabbage caused by *Erwinia carotovora*), and diseases caused by virus such as disease caused by Tobacco mosaic virus.

Plants to which the plant disease control agent for agricultural and horticultural use of the invention can be applied are not particularly limited, and can be exemplified by the plants shown below.

The plant disease control agent can be applied to grains (e.g., rice, barley, wheat, rye, oat, corn and kaoliang), beans (e.g., soybean, adzuki bean, broad bean, pea and peanut), fruit trees and fruits (e.g., apple, citrus, pear, grape, peach, Japanese apricot, cherry, walnut, almond, banana and strawberry), vegetables (e.g., cabbage, tomato, eggplant, spinach, broccoli, lettuce, onion, leek and green pepper), root vegetables (e.g., carrot, potato, sweet potato, Japanese radish, lotus root and turnip), crops to be processed (e.g., cotton, hemp, paper mulberry, mitsumata plant, rape seed, beet, hop, sugar cane, sugar beet, olive, rubber, coffee, tobacco and tea), *Cucurbitaceae* (e.g., pumpkin, cucumber, watermelon and melon), grass (e.g., orchard grass, sorghum, timothy, clover and alfalfa), turfs (e.g., Zoysia and Agrostis), crops for spice or perfume (e.g., lavender, rosemary, thyme, parsley, pepper and ginger plant), and flowers (e.g., chrysanthemum, rose and orchid).

In order to control various plant diseases, the plant disease control agent for agricultural and horticultural use to be used for the method of use of the invention may be used directly or in the form of being properly diluted with or suspended in water or the like, and may be applied according to a usual manner to seeds of an objective plant which is expected to suffer a particular disease or to a cultivation carrier for sowing the objective plant in an effective amount to control the plant disease. It can be used in an application manner such as application to a rice nursery box or application to seeds dressing, or can be used for the method of seed disinfectant, for the treatment of seedling holes or the part near plant, or for in-furrow application or application by mixing with soil. For diseases caused in field cultivation of, for example, fruit trees, grains or vegetables, the method can be conducted by treatment of coating or dipping seeds, treatment of dipping seedling roots, irrigation of carriers for cultivating seedlings such as furrows upon seeding, cultivation vessels, seedling holes or the part near plant, or by surface spraying or irrigation after mixing treatment to thereby allowing the plant to absorb the agent. It is also possible to treat a solution for hydroponics with the agent. Preferably, the agent is applied to seeds of an objective plant as seed dressing or in a manner of seed disinfectant. The agent is particularly adapted for the use as a seed treatment.

The method of treating seeds include conventional methods such as a method of forming the liquid or solid formulation of the agent into a liquid state with or without dilution and dipping seeds therein to thereby permeate the agent, a method of depositing the agent on the surface of seeds by mixing seeds with a solid or liquid formulation of the agent or by coating seeds with the powder of the formulation, a method of mixing the agent with a carrier showing a high adhesion property such as a resin or a polymer and coating seeds with it in a single- or multi-layer coat, and a method of spraying in the vicinity of seeds simultaneously with seeding.

"Seeds" to be treated means, in a broad sense, the same as "plant for breeding" and include plants for vegetative propagation such as bulbs, tubers, potatoes for breeding, discoid stems and stems for making a cutting as well as so-called seeds.

"Soil" or "cultivation carrier" in the case of conducting the method of use of the invention means a support for cultivating a plant, and is not particularly limited as to quality of its material. Any material that permits a plant to grow can be employed. Examples thereof include various so-called soils, seedling mats and water, and can also include sand, vermiculite, cotton, paper, diatomaceous earth, agar, gel-like substances, high molecular substances, rock wool, glass wool, wood chips, barks and pumice.

The method of application to soil include, for example, a method of applying the liquid or solid formulation of the agent to an area around a place of placing plant bodies or to a seed bed for cultivating seedlings with or without dilution, a method of spraying granules of the agent over an area around a place of placing plant bodies or to a seed bed for cultivating seedlings, a method of spraying a dust, wettable powder, water dispersible granule or granules before sowing or before transplanting to mix with the whole soil, and a method of spraying a dust, wettable powder, water dispersible granule or granules over planting holes or furrows before sowing or before planting plant bodies.

Regarding a method of application to a rice nursery box, formulation form may vary depending upon application stages such as sowing stage, greening stage and transplanting stage. However, the agent may be applied in the formulation form of dust, water dispersible granule or granules. Application can be performed by mixing the soil for cultivation with a dust, water dispersible granule or granules. For example, bed soil, covering soil or the whole soil can be mixed with the formulation. It is also possible to merely apply the soil for cultivation and each of the various formulations alternately in layers. As to the stage of application for sowing, formulation may be applied at any of a stage before sowing, a stage simultaneous with sowing and a stage after sowing. Application after covering with the soil is also possible.

With regard to field crops such as barley or wheat, treatment of seeds or a cultivation carrier to be in near contact with the plant is preferred. With regard to plants to be directly sowed to field, treatment of a cultivation carrier in near contact with the plant under cultivation is preferred as well as direct treatment of seeds. It is possible to conduct spray treatment using granules or irrigation treatment using the formulation in a liquid state with or without dilution.

As a treatment in the stage of sowing or cultivating seedlings of plants to be transplanted, soil drench of a seed bed for cultivating seedlings with the agent in a liquid form or spray treatment with the granules is preferred as well as direct treatment of seeds. Also, it is a preferred embodiment to apply the granules to seedling holes upon final transplanting or to mix the granules with a cultivation carrier in the vicinity of the place for transplanting the plant.

The plant disease control agent for agricultural and horticultural use to be used for the method of use of the invention is generally used in a formulation form convenient for application according to the conventional method for forming an agricultural formulation. That is, the 1,2,3-thiadiazole compound represented by formula (I) or a salt thereof is mixed with an adequate inert carrier and, if necessary, an auxiliary agent in a proper proportion to thereby dissolve, separate, suspend, mix, impregnate, adsorb or deposit, thus forming into a proper formulation such as a suspension, an emulsion, a liquid, a wettable powder, a granular formulation, a dust or tablets. For use of coating seeds, it is sufficient that the compound is formed into a formulation such as a suspension or a liquid adapted for treatment of, for example, spraying, coating or dipping.

As the inert carrier which can be used for the plant disease control agent for agricultural and horticultural use to be used in the invention, any of solid or liquid ones may be used. Examples of materials which can be the solid carrier include soybean powder, grain powder, wood powder, bark powder, sawdust, tobacco stem powder, walnut shell powder, bran, cellulose powder, residues after obtaining a plant extract, synthetic polymers such as pulverized synthetic resin, powder of inorganic minerals such as clays (e.g., kaolin, bentonite, acid clay, etc.), talcs (e.g., talc, pyrophilite, etc.), silicas (e.g., diatomaceous earth, siliceous sand, mica, white carbon (fine powder of hydrated silicon, also called hydrated silicic acid, which is synthetic, highly dispersible silisic acid; some products containing calcium silicate as a major component)), active carbon, sulfur powder, pumice, calcined diatomaceous earth, pulverized product of brisks, fly ash, sand, calcium carbonate and calcium phosphate, chemical fertilizers such as ammonium sulfate, ammonium phosphate, ammonium nitrate, urea and ammonium chloride, and compost. They are used alone or in the form of a mixture of two or more of them.

A material which can be a liquid carrier is selected from those which themselves have the dissolving ability and those which, though not having the dissolving ability, can disperse the effective ingredient compound with the aid of an auxiliary agent. Examples include the following carriers which are to be used independently or in the form of a mixture of two or more of them. That is, specific examples include water, alcohols (e.g., methanol, ethanol, isopropanol, butanol, ethylene glycol, etc.), ketones (e.g., acetone, methyl ethyl ketone, methyl isobutyl ketone, diisobutyl ketone, cyclohexanone, etc.), ethers (e.g., ethyl ether, dioxane, cellosolve, dipropyl ether, tetrahydrofuran, etc.), aliphatic hydrocarbons (e.g., kerocene, mineral oil, etc.), aromatic hydrocarbons (e.g., benzene, toluene, xylene, solvent naphtha, alkylnaphthalene, etc.), halogenated hydrocarbons (e.g., dichloroethane, chloroform, carbon tetrachloride, chlorinated benzene, etc.), esters (e.g., ethyl acetate, diisopropyl phthalate, dibutyl phthalate, dioctyl phthalate, etc.), amides (e.g., dimethylformamide, diethylformamide, dimethylacetamide, etc.), nitrites (e.g., acetonitrile etc.) and dimethylsulfoxides.

Examples of the other auxiliary agents include the following typical auxiliary agents. They are used according to purpose and are used alone or, in some cases, in combination with two or more thereof. It is also possible in some cases not to use the auxiliary agent at all. A surfactant is used for the purpose of emulsifying, dispersing, solubilizing and/or wetting the effective ingredient compound. Examples include polyoxyethylene alkyl ether, polyoxyethylene alkylaryl ether, polyoxyethylene higher fatty acid ester, polyoxyethylene resinate, polyoxyethylene sorbitan monolaurate, polyoxyethylene sorbitane monooleate, alkylarylsulfonate, naphthalenesulfonic acid condensate, lignin sulfonate and higher alcohol sulfate. Also, for the purpose of stabilizing dispersion, adhesion and/or binding of the effective ingredient compound, auxiliary agents illustrated below can be used. For example, auxiliary agents such as casein, gelatin, starch, methyl cellulose, carboxymethyl cellulose, gum arabic, polyvinyl alcohol, pine root oil, rice bran oil, bentonite and lignin sulfonate can be used.

In order to improve fluidity of a solid product, auxiliary agents illustrated below can also be used. For example, auxiliary agents such as wax, stearates and alkyl phosphates can be used. As peptiders for a suspendable product, auxiliary agents such as naphthalenesulfonic acid condensate and condensed phosphate can be used as well. As a defoaming agent, auxiliary agents such as silicone oils can be used.

In order to enlarge the scope of harmful insects to be controlled and the suitable period for controlling diseases or to reduce the amount of the chemical or attain synergistic effect, it is also possible to use the plant disease control agent for agricultural and horticultural use to be used in the invention with other insecticides, miticides, nematocides, fungicides or biocontrol products. Further, it is also possible to use the plant disease control agent for agricultural and horticultural use with a herbicide, a plant growth regulator or a fertilizer.

The plant disease control agent for agricultural and horticultural use to be used for the method of use of the invention can, if necessary, be mixed with or used together with other components. For example, upon treatment of seeds, it is possible to incorporate a repellent or other ingredient in order to prevent animals including birds from taking in the agent (including taking in by mistake). Examples of repellent include, for example, offensive smell-giving compounds such as naphthalene compounds, contact inhibitors such as castor oil, rosin, polybutane, diphenylamine pentachlorophenol, quinine, zinc oxide and aromatic solvents; bitter substances such as N-(trichloromethylthio)-4-cyclohexene-1,2-carboximide, anthraquinone, copper oxalate and terpene oil; p-dichlorobenzene; arylisothiocyanate; amyl acetate; anethole; citrus oil; cresols; herb oils such as geranium oil or lavender oil; menthol; methyl salicylate; nicotine; pentanetiol; pyridines; tributyltin chloride; thiram; ziram; carbamate series insecticides (e.g., thiocarb); guazatine; chlorinated cyclodiene series insecticides (e.g., endrin) and organophosphorus series insecticides (e.g., fenthion). As other ingredients, there can be illustrated poisonous substances or propagation inhibitors (sterilizers) such as 3-chloro-4-toluidine hydrochloride, strychnine and 20,25-diazacholesterol hydrochloride (code name: SC-12937).

The application amount of the plant disease control agent for agricultural and horticultural use to be used in the invention varies depending upon the content of the active ingredient compound, weather condition, form of formulation, stage of application, method of application, application place, disease to be controlled and kind of object plant. However, as a usual spraying formulation, it is sufficient to apply the agent in an amount properly selected from the range of from 0.1 g to 1000 g in terms of the active ingredient compound per are, preferably from the range of from 1 to 100 g. As the seed-treating agent, it is usually sufficient to apply the agent in an amount properly selected from the range of from 0.0001 to 40% by weight, preferably in the range of from 0.001 to 10% by weight in terms of the active ingredient compound based on the weight of seeds. It is usually sufficient to apply the agent in an amount properly selected from the range of from 0.1 to 1000 g, preferably from the range of from 1 to 50 g in terms of the active ingredient compound per are. Also, it is sufficient to apply in an amount of from about 0.0001 to about 10% by weight based on the weight of a carrier for cultivation. When it is applied as an emulsion, wettable powder, suspension or liquid formulation by diluting with water, the application concentration is from 0.001 to 70% by weight as the active ingredient. A granular formulation, a dust or, in the case of treating seeds, a liquid formulation may usually be applied as such without dilution.

EXAMPLES

Next, specific descriptions are given below by reference to Examples which, however, are not to be construed as limiting the invention so long as they are within the gist of the invention.

Example 1

Production of (2-chlorobenzyl)4-cyclopropyl-1,2,3-thiadiazole-5-carboxylate (Compound No. 1-10)

4-Cyclopropyl-1,2,3-thiadiazolecarboxylic acid (1 g; 5.9 mmols), 2-chloro-1-methylpyridinium iodide (1.8 g; 7.0 mmols), triethylamine (1.5 g; 15 mmols) and 2-chlorobenzyl alcohol (0.92 g; 6.5 mmols) were dissolved or suspended in THF (15 ml), followed by stirring at room temperature for 10 hours. After removing insoluble materials by filtration, the filtrate was concentrated under reduced pressure, and the residue was purified by silica gel column chromatography (hexane:ethyl acetate=10:1) to thereby obtain 1.5 g of(2-chlorobenzyl)4-cyclopropyl-1,2,3-thiadiazole-5-carboxylate.

Yield: 89%

Physical properties: mp. 54° C.

Example 2

Production of 3'-chloro-4-cyclopropyl-4'-methyl-1,2,3-thiadiazole-5-carboxanilide (Compound No. 1-95)

4-Cyclopropyl-1,2,3-thiadiazolecarboxylic acid (4 g; 24 mmols), 2-chloro-1-methylpyridinium iodide (7.2 g; 28 mmols), triethylamine (5.9 g; 58 mmols) and 3-chloro-4- methylaniline (3.7 g; 26 mmols) were dissolved or suspended in THF (50 ml), followed by stirring at room temperature for 10 hours. Water was added thereto to stop the reaction, the mixture was extracted with ethyl acetate. After drying over anhydrous sodium sulfate, the solvent was concentrated under reduced pressure, and the residue was purified by silica gel column chromatography (hexane:ethyl acetate=3:1) to thereby obtain 6.9 g of 3'-chloro-4-cyclopropyl-4'-methyl-1,2,3-thiadiazole-5-carboxanilide.
Yield: 99%
Physical properties: mp. 150-153° C.

Example 3

Production of 2-(4-cyclopropyl-1,2,3-thiadiazol-5-ylcarbonylamino)benzoic acid (Compound No. 1-98)

Thionyl chloride (4 ml) was added to 4-cyclopropyl-1,2,3-thiadiazolecarboxylic acid (0.6 g; 3.5 mmols) and, after refluxing for 2 hours under heating, the mixture was cooled and concentrated under reduced pressure to obtain 4-cyclopropyl-1,2,3-thiadiazole-5-carboxylic acid chloride. Subsequently, the mixture was dissolved in THF (2 ml), and was gradually added to a solution of sodium hydroxide (0.14 g; 3.5 mmols) and anthranilic acid (0.48 g; 3.5 mols) in water (7 ml). After stirring at room temperature for 4 hours, concentrated hydrochloric acid was added to acidify the solution. Crystals thus formed were collected by filtration. The thus-obtained crystals were washed with water and methanol to obtain 0.77 g of 2-(4-cyclopropyl-1,2,3-thiadiazole-5-carbonylamino)benzoic acid.
Yield: 76%
Physical properties: $^1$H-NMR (TMS, δ value ppm; solvent: DMSO-d6) 1.2-1.35 (m, 4H), 2.7-2.9 (m, 1H), 7.30 (m, 2H), 7.70 (t, 1H), 8.05 (d, 1H), 8.46 (d, 1H), 11.95 (br, 1H)

Example 4

Production of 2'-cyano-4-cyclopropyl-1,2,3-thiadiazole-5-carboxanilide (Compound No. 1-100)

4-Cyclopropyl-1,2,3-thiadiazolecarboxylic acid (0.5 g; 2.9 mmols), 1-ethyl-3-(3'-dimethylaminopropyl)carbodiimide hydrochloride (0.62 g; 3.2 mmols) and 2-cyanoaniline (0.38 g; 3.2 mmols) were dissolved or suspended in THF (15 ml), followed by stirring at room temperature for 10 hours. Subsequently, water was added thereto, and the mixture was extracted with ethyl acetate. The organic layer was washed with successively a saturated aqueous sodium hydrogencarbonate solution and a saturated aqueous sodium chloride solution. After drying over anhydrous magnesium sulfate, the solution was concentrated under reduced pressure, and the residue was purified by silica gel column chromatography (hexane:ethyl acetate=3:1) to thereby obtain 0.53 g of 2'-cyano-4-cyclopropyl-1,2,3-thiadiazole-5-carboxanilide.
Yield: 68%
Physical properties: mp. 124° C.

Example 5

Production of 4-cyclopropyl-1,2,3-thiadiazole-5-carbohydrazide (Compound No. 1-115)

Hydrazine monohydrate (1.75 g; 35 mmols) was dissolved in ethanol (15 ml), and methyl 4-cyclopropyl-1,2,3-thiadiazole-5-carboxylate (1.29 g; 7 mmols) was added thereto, followed by stirring at room temperature for 10 hours. Ethanol was evaporated under reduced pressure and, after adding thereto water, the reaction mixture was extracted with ethyl acetate. The organic layer was washed with a saturated aqueous sodium chloride solution and dried over anhydrous sodium sulfate, the solvent was evaporated. The residue was washed with a mixed solvent of hexane-ethyl acetate to obtain 1.2 g of 4-cyclopropyl-1,2,3-thiadiazole-5-carbohydrazide.
Yield: 95%
Physical properties: $^1$H-NMR(TMS, δ value ppm; solvent: DMSO-d6) 1.12-1.30 (m, 4H), 3.30-3.45 (m, 1H), 4.73-5.25 (br, 2H), 9.42-10.04 (br, 1H)

Example 6

Production of N'-(4-cyclopropyl-1,2,3-thiadiazol-5-ylcarbonyl)hydrazonobenzaldehyde (Compound No. 1-117)

4-Cyclopropyl-1,2,3-thiadiazole-5-carbohydrazide (1.22 g; 6.6 mmols) was dissolved in methanol (30 ml), and benzaldehyde (0.72 g; 6.8 mmols) and 2 drops of concentrated sulfuric acid were added thereto, followed by stirring the solution at room temperature for 10 hours. Methanol was evaporated under reduced pressure and, after adding water thereto, the mixture was extracted with ethyl acetate. The organic layer was washed with successive, a saturated aqueous sodium bicarbonate solution and a saturated aqueous sodium chloride solution and, after drying over anhydrous sodium sulfate, the solvent was evaporated under reduced pressure. The residue was washed with a mixed solvent of hexane-ethyl acetate to thereby obtain N'-(4-cyclopropyl-1,2,3-tiadiazol-5-ylcarbonyl)hydrazonobenzaldehyde (1.71 g; 95%)
Yield: 95%
Physical properties: mp. 230-239° C.

Example 7

Production of N'-(4-cyclopropyl-1,2,3-thiadiazol-5-ylcarbonyl)-N'-methylhydrazonobenzaldehyde (Compound No. 1-118)

N'-Benzylidene-4-cyclopropyl-1,2,3-thiadiazole-5-carbohydrazide (0.95 g; 3.5 mmols) was dissolved in dimethylformamide (30 ml), and potassium carbonate (0.55 g; 4 mmols) and methyl iodide (0.99 g; 7 mmols) were added thereto, followed by stirring the mixture at room temperature for 5 hours. After adding water thereto, the mixture was extracted with ethyl acetate, and the organic layer was washed 4 times with water, then with a saturated aqueous sodium chloride solution, followed by drying over anhydrous sodium sulfate. After the mixture was concentrated under reduced pressure, the residue was washed with a mixed solvent of hexane-ethyl acetate to thereby obtain 0.95 g of N'-(4-cyclopropyl-1,2,3-thiadiazol-5-ylcarbonyl)-N'-methylhydrazonobenzaldehyde.
Yield: 95%
Physical properties: mp. 159.0-160.5° C.

Example 8

Production of 3'-chloro-4-cyclopropyl-4'-methyl-1,2,3-thiadiazole-5-thiocarboxamilide (Compound No. 1-143)

3'-Chloro-4-cyclpropyl-4'-methyl-1,2,3-thiadiazole-5-carboxanilide (0.5 g; 1.7 mmols) and Lauesson's reagent (1 g;

2.5 mmols) were dissolved in toluene (10 ml), followed by refluxing for 3 hours under heating. After cooling to room temperature, water was added thereto, and the mixture was extracted with ethyl acetate. After drying over anhydrous sodium sulfate, the solvent was concentrated under reduced pressure, and the residue was purified by silica gel column chromatography (hexane:ethyl acetate=5:1) to thereby obtain 5.0 g of 3'-chloro-4-cyclopropyl-4'-methyl-1,2,3-thiadiazole-5-thiocarboxanilide.

Yield: 95%

Physical properties: refractive index $n_D$ 1.6698 (22° C.)

Example 9

Production of 4-cyclopropyl-1,2,3-thiadiazole-5-carbonitrile (Compound No. 3-1)

4-Cyclopropyl-1,2,3-thiadiazole-5-carboxamide (4 g; 24 mmols) was dissolved in toluene (15 ml), and thionyl chloride (5 ml) was added thereto, followed by refluxing for 10 hours under heating. After cooling to room temperature, ice was added thereto to stop the reaction, and sodium hydrogen carbonate was added thereto to neutralize, followed by extracting with ethyl acetate. After drying over anhydrous sodium sulfate, the solvent was concentrated under reduced pressure, and the residue was purified by silica gel column chromatography (hexane:ethyl acetate=20:1) to thereby obtain 2.1 g of 4-cyclopropyl-1,2,3-thiadiazole-5-carbonitrile.

Yield: 58%

Physical properties: refractive index $n_D$ 1.5716 (26° C.)

Example 10

Production of 2-(4-cyclopropyl-1,2,3-thiadiazol-5-yl)-4-H-3,1-benzoxazin-4-one (Compound No. 2-1)

2-(4-Cyclopropyl-1,2,3-thiadiazol-5-ylcarbonylamino) benzoic acid (0.77 g; 2.7 mmols), triethylamine (0.54 g; 5.3 mmols) and 2-chloro-1-methylpyridinium iodide (0.82 g; 3.2 mmols) were dissolved or suspended in THF (15 ml), followed by stirring at room temperature for 10 hours. Subsequently, insoluble materials were removed by filtration, and the filtrate was concentrated under reduced pressure. Crystals thus formed were washed with methanol to obtain 0.63 g of 2-(4-cyclopropyl-1,2,3-thiadiazol-5-yl)-4H-3,1-benzoxazin-4-one.

Yield: 87%

Physical properties: mp. 164-165° C.

Reference Example 1

Production of methyl 3-cyclopropyl-3-oxopropionate

Merdramic acid (50 g; 347 mmols) was dissolved in chloroform (550 ml), and pyridine (56 g; 700 mmols) was added thereto. Subsequently, a solution of cyclopropanecarboxylic acid chloride (40 g; 383 mmols) in chloroform (50 ml) was added dropwise thereto at a temperature of 10° C. or lower while cooling in an ice-bath. After completion of the dropwise addition, the mixture was stirred for further 1 hour under cooling in the ice-bath, then at room temperature for 1 hour. Subsequently, after cooling again using the ice-bath, 1N—HCL aqueous solution (500 ml) was added thereto. The reaction product was extracted with chloroform, washed with water, and dried over anhydrous sodium sulfate, followed by concentrating under reduced pressure. Then, methanol (500 ml) was added thereto to dissolve the residue, and the solution was heated for 3 hours under reflux. After cooling to room temperature, the solvent was distilled off under reduced pressure, and the residue was distilled to obtain 40 g of methyl 3-cyclopropyl-3-oxopropionate.

Yield: 80%

Physical properties: bp. 80° C. (10 mmHg)

Reference Example 2

Production of methyl 4-cyclopropyl-1,2,3-thiadiazole-5-carboxylate

Methyl 3-cyclopropyl-3-oxopropionate (10 g; 70 mmols) was dissolved in methanol (100 ml), and methyl carbazinate (6.3 g; 70 mmols) and p-toluenesulfonic acid (20 mg; 0.11 mol) were added thereto. After stirring the mixture overnight, methanol was evaporated under reduced pressure. Subsequently, toluene (10 ml) was added thereto, and thionyl chloride (20 ml) was gradually added dropwise thereto under cooling in an ice-bath. After completion of the dropwise addition, the mixture was stirred for 4 hours at room temperature, then poured onto ice to stop the reaction, and neutralized with sodium hydrogencarbonate. After extracting with ethyl acetate and washing with a saturated sodium chloride aqueous solution, the solution was dried over anhydrous sodium sulfate. After the mixture was concentrated under reduced pressure, the residue was purified by silica gel column chromatography (hexane:ethyl acetate=10:1) to thereby obtain 9 g of methyl 4-cyclopropyl-1,2,3-thiadiazole-5-carboxylate.

Yield: 70%

Physical properties: mp. 47° C.

Reference Example 3

Production of 4-cyclopropyl-1,2,3-thiadiazole-5-carboxylic acid

Methyl 4-cyclopropyl-1,2,3-thiadiazole-5-carboxylate (35 g; 190 mmols) was dissolved in methanol (150 ml), and an aqueous solution (150 ml) of sodium hydroxide (15 g; 360 mmols) was added dropwise thereto over 30 minutes under cooling in an ice-bath. After completion of the dropwise addition, the mixture was stirred for 2 hours at room temperature, and methanol was evaporated under reduced pressure, followed by washing with ethyl acetate. The aqueous layer was acidified by using concentrated hydrochloric acid, and was extracted with ethyl acetate. The organic layer was dried over anhydrous sodium sulfate, and then the solvent was evaporated under reduced pressure. The residue was washed with a mixed solvent of hexane-ethyl acetate to thereby obtain 28 g of 4-cyclopropyl-1,2,3-thiadiazole-5-carboxylic acid.

Yield: 86%

Physical properties: mp. 158-159° C.

Reference Example 4

Production of 4-cyclopropyl-1,2,3-thiadiazole-5-carboxamide

Methyl 4-cyclopropyl-1,2,3-thiadiazole-5-carboxylate (2 g; 11 mmols) was dissolved in methanol (5 ml), and aqueous ammonia (5 ml) was added thereto, followed by stirring at room temperature for 1 hour. Subsequently, the reaction mixture was concentrated under reduced pressure, and the residue was washed with hexane to obtain 1 g of 4-cyclopropyl-1,2,3-thiadiazole-5-carboxamide.

Yield: 55%

Physical properties: mp. 163° C.

Typical formulation examples and test examples of the invention will be described below which, however, do not limit the invention. Additionally, in the formulation examples, "parts" are by weight.

Formulation Example 1

| | |
|---|---|
| Compound of the invention | 10 parts |
| Xylene | 70 parts |
| N-Methylpyrrolidone | 10 parts |
| Mixture of polyoxyethylene nonylphenyl ether and calcium alkylbenzenesulfonate | 10 parts |

They are uniformly mixed and dissolved to form an emulsion.

Formulation Example 2

| | |
|---|---|
| Compound of the invention | 3 parts |
| Clay powder | 82 parts |
| Diatomaceous earth powder | 15 parts |

They are uniformly mixed and pulverized to form a dust formulation.

Formulation Example 3

| | |
|---|---|
| Compound of the invention | 5 parts |
| Mixed powder of bentonite and clay | 90 parts |
| Calcium lignin sulfonate | 5 parts |

They are uniformly mixed, and a suitable amount of water is added thereto by kneading, followed by granulating and drying to thereby form a granular formulation.

Formulation Examples

| | |
|---|---|
| Compound of the invention | 20 parts |
| Kaolin and synthetic highly dispersible silicic acid | 75 parts |
| Mixture of polyoxyethylene nonylphenyl ether and calcium alkylbensenesulfonate | 5 parts |

They are uniformly mixed and pulverized to form a wettable powder.

Test Example 1

Test on Controlling Effect by Seed Dressing Against Wheat Powdery Mildew

Seeds of wheat (cultivar: chihoku komugi) and a wettable powder prepared according to Formulation Example were placed in a vinyl bag, followed by adding thereto a small volume of water, and they were mixed to conduct seed dressing. On the day after this treatment, the seeds sowed in a plastic pot of 10 cm diameter, and cultivated in a greenhouse. Twenty five days after sowing, the seedlings thus obtained were inoculated with powdery mildew fungus (*Blumeria graminis*) by sprinkling. Seven days after inoculation, the seedlings were investigated and infection index was estimated according to the criterion shown below, after which the control efficacy (%) was calculated. In this occasion, infection index on the untreated plot was 8.0. As comparative examples, the following compounds described in JP-A-2001-10909 were evaluated.

I: 3'-chloro-4,4'-dimethyl-1,2,3-thiadiazole-5-carboxanilide

II: benzyl 4-isopropyl-1,2,3-thiadiazole-5-carboxylate

III: methyl 4-cyclopropyl-1,2,3-thiadiazole-5-carboxylate

IV: 4-cyclopropyl-1,2,3-thiadiazole-5-carboxylic acid

Infection Index

0: No infection.

0.5: Lesion area percentage: less than 10%

1: Lesion area percentage; 10 to less than 20%

2: Lesion area percentage; 20 to less than 30%

3: Lesion area percentage; 30 to less than 40%

4: Lesion area percentage; 40 to less than 50%

5: Lesion area percentage; 50 to less than 60%

6: Lesion area percentage; 60 to less than 70%

7: Lesion area percentage; 70 to less than 80%

8: Lesion area percentage; 80 to less than 90%

9: Lesion area percentage; 90 to less than 100%

10: Lesion area percentage; 100%

Control efficacy (%)={1-(infection index on treated plot/infection index on untreated plot)}×100

Rank of Control Efficacy

A: Control efficacy 100-90%

B: Control efficacy 89-80%

C: Control efficacy 79-60%

D: Control efficacy 59-0%

As a result of the above-described test, the compounds shown in Tables 1, 2 and 3 were found to show an excellent controlling effect against wheat powdery mildew (*Blumeria graminis*) in the treating amount (0.15% in terms of the active ingredient based on the weight of dry seeds). In particular, each of the compounds of 1-8, 1-10, 1-11, 1-12, 1-13, 1-15, 1-16, 1-18, 1-24, 1-25, 1-26, 1-30, 1-41, 1-44, 1-47, 1-50, 1-53, 1-56, 1-59, 1-62, 1-63, 1-65, 1-66, 1-68, 1-82, 1-95, 1-96, 1-97, 1-98 1-103, 1-110, 1-111, 1-112, 1-113, 1-119, 1-120, 1-121, 1-122, 1-124, 1-143, 1-144, 1-145, 1-151, 1-152, 1-153, 1-154, 1-155, 1-156, 1-157, 1-158, 1-162, 1-163, 1-164, 1-165, 1-166, 1-167, 1-168, 1-169, 1-170, 1-173, 1-174, 1-175, 1-176, 1-177, 1-178, 1-179, 1-180, 1-181, 1-182, 1-183, 1-184, 1-185, 1-186, 1-189, 1-190, 2-1 and 3-1 was ranked B or more.

Comparative compounds I, III and IV showed a control efficacy ranked B in the treating amount (0.15% in terms of the active ingredient based on the weight of dry seeds), but comparative compound II showed a control efficacy ranked C.

Test Example 2

Test on Controlling Effect by Seed Dressing Against Wheat Powdery Mildew

Test on Long-Lasting Effect

Seeds of wheat (cultivar: *Chihoku Komugi*) and a wettable powder prepared according to Formulation Example were placed in a vinyl bag, followed by adding thereto a small volume of water, and they were mixed to conduct seed dressing. On the day after this treatment, the seeds sowed in a plastic pot of 10 cm diameter, and cultivated in a greenhouse. Fifty days after sowing, the seedlings thus obtained were inoculated with powdery mildew fungus (*Blumeria graminis*) by sprinkling. Seven days after inoculation, the seedlings were investigated and infection index was estimated according to the criterion shown below, after which the control efficacy (%) was calculated. In this occasion, infection index on the untreated plot was 8.0. As comparative examples, the above-described compounds I, II, III and IV were evaluated.

As a result of the above-described test, the compounds shown in Tables 1, 2 and 3 were found to show an excellent controlling effect against wheat powdery mildew (*Blumeria graminis*) in the treating amount (0.15% in terms of the active ingredient based on the weight of dry seeds). In particular, each of the compounds of 1-8, 1-10, 1-11, 1-12, 1-13, 1-15, 1-16, 1-18, 1-24, 1-30, 1-41, 1-44, 1-50, 1-53, 1-62, 1-63, 1-68, 1-82, 1-95, 1-96, 1-97, 1-98, 1-110, 1-111, 1-112, 1-113, 1-119, 1-121, 1-124, 1-143, 1-144, 1-145, 1-155, 1-156, 1-165, 1-166, 1-167, 1-169, 1-170, 1-173, 1-175, 1-176, 1-177, 1-178, 1-179, 1-183, 1-184, 1-189, 1-190, 2-1 and 3-1 was ranked B or more. Further, each of compounds 1-8, 1-11, 1-12, 1-24, 1-30, 1-44, 1-53, 1-63, 1-95, 1-96, 1-98, 1-110, 1-119, 1-121, 1-166 and 2-1 was found to show a control efficacy ranked A.

Comparative compound IV showed a control efficacy ranked B in the treating amount (0.15% in terms of the active ingredient based on the weight of dry seeds), but comparative compounds I, II and III showed a control efficacy ranked D in the treating amount (0.15% in terms of the active ingredient based on the weight of dry seeds), thus being clearly inferior to the compounds of the invention.

Test Example 3

Test on Phytotoxicity for Wheat by Treatment of Seeds

Safety Test on Plant

Seeds of wheat (cultivar: *Chihoku Komugi*) and a wettable powder prepared according to Formulation Example were placed in a vinyl bag, followed by adding thereto a small volume of water, and they were mixed to conduct seed dressing. On the day after this treatment, the seeds sowed in a plastic pot of 10 cm diameter, and cultivated in a greenhouse. Seven days and fourteen days after sowing, phytotoxicity for germination of the seeds and growth at the early stage were evaluated. As a comparative example, the comparative compound IV which showed a control efficacy ranked B in Test Example 2 was used for evaluation.

As a result of the above-described test, it was found that the compounds of the invention which showed a control efficacy ranked A in Test Example 2, 1-8, 1-11, 1-12, 1-24, 1-30, 1-44, 1-53, 1-63, 1-95, 1-96, 1-98, 1-110, 1-119, 1-121 and 1-166 exerted absolutely no phytotoxicity in the treating amount (0.15% in terms of the active ingredient based on the weight of dry seeds).

The comparative compound IV was found to delay germination and suppressed growth in the treating amount (0.15% in terms of the active ingredient based on the weight of dry seeds).

As is different from the conventional art, the compounds of the invention are intended to control diseases for an extremely long period of from the highest growth stage to the later stage only by applying to seeds of the object plant or to a cultivation carrier for sowing the objective plant. For this purpose, a long-lasting effect and, further, a safety for object plants are required in addition to an excellent control efficacy. The compounds of the invention have all of such factors. As is apparent from the above-described Test examples 1 to 3, the thiadiazole compounds described in JP-A-2001-10909 do not have them at the same time.

Although the invention has been described in detail by reference to specific embodiments, it is apparent to those skilled in the art that various changes and modifications can be made without departing from the spirit and the scope of the invention.

Additionally, this application is based on the Japanese patent application (Japanese Patent Application No. 2005-49431) filed on Feb. 24, 2005 and the Japanese patent application (Japanese Patent Application No. 2005-263617) filed on Sep. 12, 2005, and the entire contents thereof being hereby incorporated by reference.

INDUSTRIAL APPLICABILITY

The invention can provide plant disease control agent for agricultural and horticultural use which have an excellent performance, particularly an excellent safety for object plants and an excellent controlling effect in comparison with the conventional art, and which show an extremely long-lasting effect, and a method of using the controlling agent more effectively.

The invention claimed is:

1. A 1,2,3-thiadiazole compound selected from the group consisting of (2-chlorobenzyl) 4-cyclopropyl-1,2,3-thiadiazole-5-carboxylate, (3-chlorobenzyl) 4-cyclopropyl-1,2,3-thiadiazole-5-carboxylate, (4-chlorobenzyl) 4-cyclopropyl-1,2,3-thiadiazole-5-carboxylate, (4-chloro-α-methylbenzyl) 4-cyclopropyl-1,2,3-thiadiazole-5-carboxylate, (4-methoxycarbonylbenzyl) 4-cyclopropyl-1,2,3-thiadiazole-5-carboxylate, N-benzyl-4-cyclopropyl-1,2,3-thiadiazole-5-carboxamide, N-(4-t-butylbenzyl)-4-cyclopropyl-1,2,3-thiadiazole-5-carboxamide, 3'-chloro-4-cyclopropyl-4'-methyl-1,2,3-thiadiazole-5-carboxanilide, 4-cyclopropyl-2',4'-dimethoxy-1,2,3-thiadiazole-5-carboxanilide, 4-cyclopropyl-3',4'-dimethoxy-1,2,3-thiadiazole-5-carboxanilide, 2'-carboxy-4-cyclopropyl-1,2,3-thiadiazole-5-carboxanilide, N-(4-isobutylthiazol-2-yl)-4-cyclopropyl-1,2,3-thiadiazole-5-carboxamide, N-phenylsulfonyl-4-cyclopropyl-1,2,3-thiadiazole-5-carboxamide, and N-(3,4-dimethoxybenzyl)-4-cyclopropyl-1,2,3-thiadiazole-5-carboxamide, or a salt thereof.

2. A plant disease control agent for agricultural and horticultural use, which comprises as an active ingredient the 1,2,3-thiadiazole compound according to claim 1, or a salt thereof.

3. A plant disease control agent for agricultural and horticultural use for sterilizing seeds, which comprises as an active ingredient one or two or more compounds selected from 1,2,3-thiadiazole compounds according to claim 1, or a salt thereof.

4. A method of controlling plant disease, which comprises treating a seed of an objective plant or a cultivation carrier for sowing an objective plant with an effective amount of the plant disease control agent according to claim 3.

5. The method according to claim 4, wherein the seed of an objective plant is treated.

6. The method according to claim 5, wherein the effective amount is from 0.0001 to 40% by weight based on the weight of the seed of an objective plant.

7. The method according to claim 4, wherein the cultivation carrier for sowing an objective plant is treated.

8. The method according to claim 7, wherein the effective amount is from 0.0001 to 10% by weight based on the weight of the cultivation carrier for sowing an objective plant.

9. The 1,2,3-thiadiazole compound according to claim 1, which is (2-chlorobenzyl) 4-cyclopropyl-1,2,3-thiadiazole-5-carboxylate, or a salt thereof.

10. The 1,2,3-thiadiazole compound according to claim 1, which is (3-chlorobenzyl) 4-cyclopropyl-1,2,3-thiadiazole-5-carboxylate, or a salt thereof.

11. The 1,2,3-thiadiazole compound according to claim 1, which is (4-chlorobenzyl) 4-cyclopropyl-1,2,3-thiadiazole-5-carboxylate, or a salt thereof.

12. The 1,2,3-thiadiazole compound according to claim 1, which is (4-chloro-α-methylbenzyl) 4-cyclopropyl-1,2,3-thiadiazole-5-carboxylate, or a salt thereof.

13. The 1,2,3-thiadiazole compound according to claim 1, which is (4-methoxycarbonylbenzyl) 4-cyclopropyl-1,2,3-thiadiazole-5-carboxylate, or a salt thereof.

14. The 1,2,3-thiadiazole compound according to claim 1, which is N-benzyl-4-cyclopropyl-1,2,3-thiadiazole-5-carboxamide, or a salt thereof.

15. The 1,2,3-thiadiazole compound according to claim 1, which is N-(4-t-butylbenzyl)-4-cyclopropyl-1,2,3-thiadiazole-5-carboxamide, or a salt thereof.

16. The 1,2,3-thiadiazole compound according to claim 1, which is 3'-chloro-4-cyclopropyl-4'-methyl-1,2,3-thiadiazole-5-carboxanilide, or a salt thereof.

17. The 1,2,3-thiadiazole compound according to claim 5, which is 4-cyclopropyl-2',4'-dimethoxy-1,2,3-thiadiazole-5-carboxanilide, or a salt thereof.

18. The 1,2,3-thiadiazole compound according to claim 1, which is 4-cyclopropyl-3',4'-dimethoxy-1,2,3-thiadiazole-5-carboxanilide, or a salt thereof.

19. The 1,2,3-thiadiazole compound according to claim 5, which is 2'-carboxy-4-cyclopropyl-1,2,3-thiadiazole-5-carboxanilide, or a salt thereof.

20. The 1,2,3-thiadiazole compound according to claim 1, which is N-(4-isobutylthiazol-2-yl)-4-cyclopropyl-1,2,3-thiadiazole-5-carboxamide, or a salt thereof.

21. The 1,2,3-thiadiazole compound according to claim 1, which is N-phenylsulfonyl-4-cyclopropyl-1,2,3-thiadiazole-5-carboxamide, or a salt thereof.

22. The 1,2,3-thiadiazole compound according to claim 1, which is N-(3,4-dimethoxybenzyl)-4-cyclopropyl-1,2,3-thiadiazole-5-carboxamide, or a salt thereof.

* * * * *